(12) United States Patent
Karsdal et al.

(10) Patent No.: US 10,232,021 B2
(45) Date of Patent: Mar. 19, 2019

(54) CALCITONIN MIMETICS FOR TREATING DISEASES AND DISORDERS

(71) Applicant: KEYBIOSCIENCE AG, Stans (CH)

(72) Inventors: Morten Karsdal, Kobenhavn O (DK); Kim Henriksen, Hillerod (DK); Kim Vietz Andreassen, Ballerup (DK)

(73) Assignee: KeyBioscience AG, Stans (CH)

( * ) Notice: Subject to any disclaimer, the term of this patent is extended or adjusted under 35 U.S.C. 154(b) by 0 days.

(21) Appl. No.: 15/036,475

(22) PCT Filed: Nov. 10, 2014

(86) PCT No.: PCT/EP2014/074207
§ 371 (c)(1),
(2) Date: May 13, 2016

(87) PCT Pub. No.: WO2015/071229
PCT Pub. Date: May 21, 2015

(65) Prior Publication Data
US 2017/0143800 A1   May 25, 2017

(30) Foreign Application Priority Data

Nov. 14, 2013 (GB) .................................. 1320112.4
Aug. 19, 2014 (GB) .................................. 1414706.0

(51) Int. Cl.
| | | |
|---|---|---|
| C07K 14/585 | (2006.01) |
| A61K 38/23 | (2006.01) |
| A61K 45/06 | (2006.01) |
| A61K 31/155 | (2006.01) |
| A61K 9/00 | (2006.01) |
| A61K 9/50 | (2006.01) |
| A61K 47/12 | (2006.01) |
| A61K 38/00 | (2006.01) |

(52) U.S. Cl.
CPC ............ *A61K 38/23* (2013.01); *A61K 9/0053* (2013.01); *A61K 9/50* (2013.01); *A61K 31/155* (2013.01); *A61K 45/06* (2013.01); *A61K 47/12* (2013.01); *C07K 14/585* (2013.01); *A61K 38/00* (2013.01)

(58) Field of Classification Search
None
See application file for complete search history.

(56) References Cited

U.S. PATENT DOCUMENTS

| | | |
|---|---|---|
| 4,708,934 A | 11/1987 | Gilligan et al. |
| 5,102,666 A | 4/1992 | Acharya |
| 5,438,040 A | 8/1995 | Ekwuribe et al. |
| 5,773,647 A | 6/1998 | Leone-Bay |
| 5,866,536 A | 2/1999 | Leone-Bay et al. |
| 5,912,014 A | 6/1999 | Stern et al. |
| 6,086,918 A | 7/2000 | Stern et al. |
| 6,673,574 B2 | 1/2004 | Stern et al. |
| 7,189,414 B2 | 3/2007 | Rubinstein et al. |
| 7,268,214 B2 | 9/2007 | O'Mahony et al. |
| 7,316,819 B2 | 1/2008 | Crotts et al. |
| 7,445,911 B2 | 11/2008 | Consalvo et al. |
| 8,093,207 B2 | 1/2012 | Stern et al. |
| 2002/0115592 A1 | 8/2002 | New et al. |
| 2003/0069170 A1 | 4/2003 | Soltero et al. |
| 2006/0292672 A1 | 12/2006 | Miller et al. |
| 2007/0238707 A1 | 10/2007 | Leonard et al. |
| 2008/0200563 A1 | 8/2008 | Hoffer et al. |
| 2009/0074824 A1 | 3/2009 | Pena et al. |
| 2009/0087479 A1 | 4/2009 | Lau et al. |
| 2009/0317462 A1 | 12/2009 | Stern et al. |

FOREIGN PATENT DOCUMENTS

| | | |
|---|---|---|
| EP | 0308067 A2 | 3/1989 |
| EP | 0382403 A2 | 8/1990 |
| WO | 200059863 A1 | 10/2000 |
| WO | 200228436 A1 | 4/2002 |
| WO | 2004084870 A1 | 10/2004 |
| WO | 2004091584 A1 | 10/2004 |
| WO | 2005014031 A1 | 2/2005 |
| WO | 2005094785 A2 | 10/2005 |
| WO | 2007029238 A2 | 3/2007 |

(Continued)

OTHER PUBLICATIONS

Amino Acids, Promega Technical Reference, Part GE626 (2010), 1 page.*
Diabetes, from http://www.merckmanuals.com/professional/endocrine-and-metabolic-disorders/ . . . , pp. 1-34, accessed Sep. 2, 2016.*
Cornier et al., "The metabolic syndrome," Endo. Rev. 29:777-822 (2008).*
Chestnut et al., "Salmon calcitonin: a review of current and future therapeutic indications," Osteoporos Int 19:479-491 (2008).*
Rheumatoid arthritis, accessed Oct. 24, 2017 at URL merckmanuals.com/professional/musculoskeletal-and-connective-tissue-disorders (pp. 1-26).*
Chalasani et al., "The Diagnosis and Management of Non-Alcoholic Fatty Liver Disease: Practice Guideline by the American Association for the Study of Liver Diseases, American College of Gastroenterology, and the American Gastroenterological Association," Hepatology 55:2005-2023 (2012).*

(Continued)

*Primary Examiner* — Julie Ha
*Assistant Examiner* — Kristina M Hellman
(74) *Attorney, Agent, or Firm* — Benjamin Aaron Adler

(57) ABSTRACT

Calcitonin mimetic peptides having an amino acid sequence in accordance with SEQ ID NO:8 or SEQ ID NO:53, each of which may be carboxylated at its N-terminal or otherwise modified to reduce the positive charge of the first amino acid and independently of that may be amidated at its C-terminal, and in each of which the 1 and 7 position cysteine residues may together be replaced by α-aminosuberic acid (Asu) are useful as medicaments for treating diabetes (Type I and/or Type II), excess bodyweight, excessive food consumption, metabolic syndrome, rheumatoid arthritis, non-alcoholic fatty liver disease, osteoporosis, or osteoarthritis, poorly regulated blood glucose levels, poorly regulated response to glucose tolerance tests, or poorly regulated of food intake.

Figure 1A:
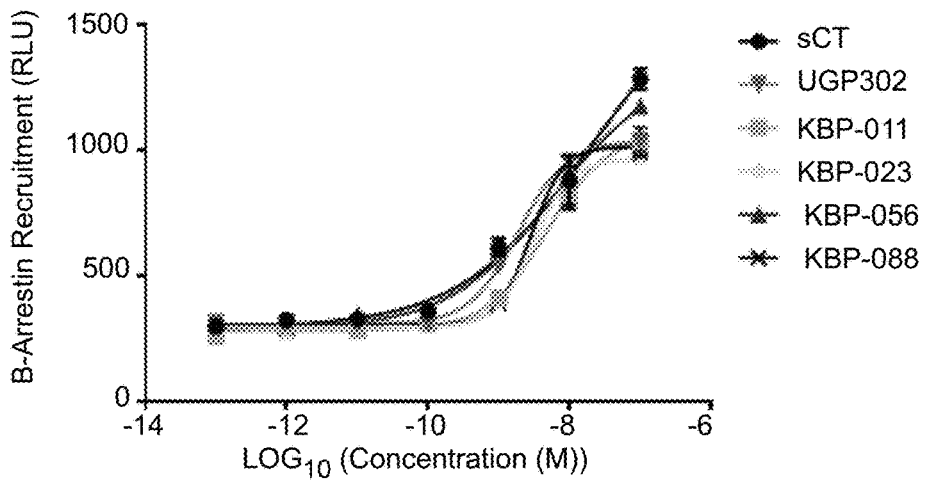
Figure 1B:
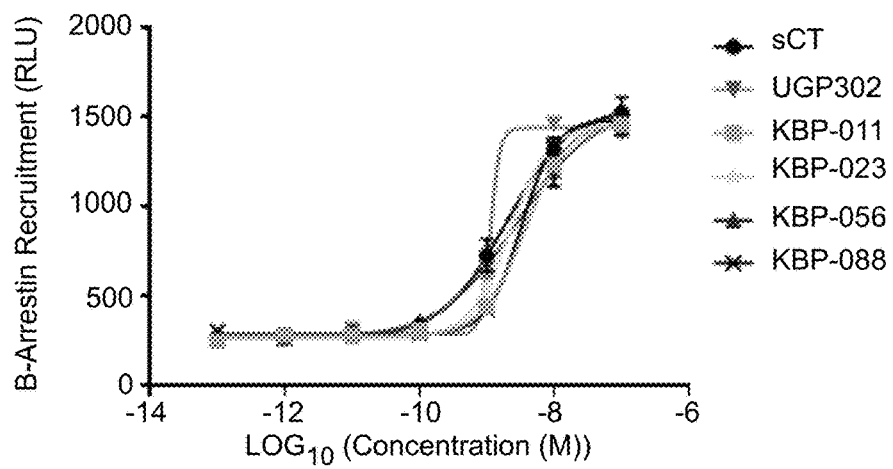
Figure 1C:
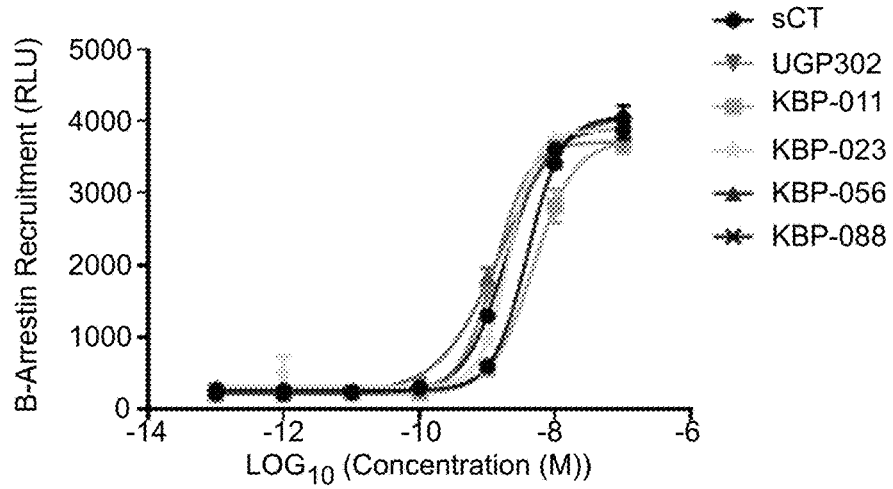
Figure 1D:
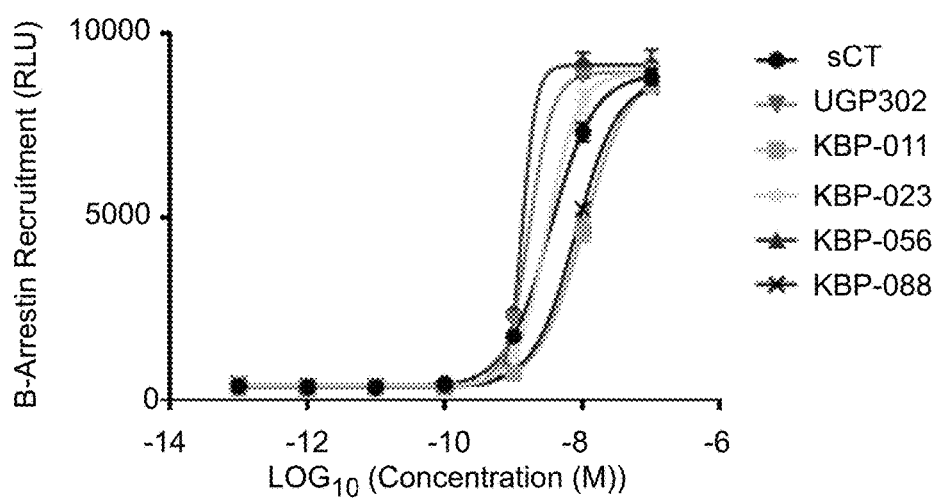
Figure 1E:
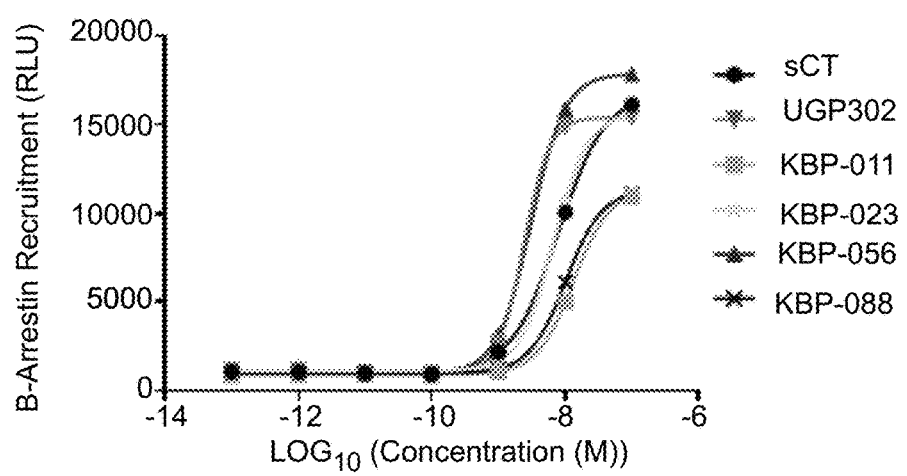

12 Claims, 11 Drawing Sheets
Specification includes a Sequence Listing.

(56) References Cited

FOREIGN PATENT DOCUMENTS

WO        2013067357 A1      5/2013

OTHER PUBLICATIONS

Ray et al. Production of recombinant salmon calcitonin by in vitro amidation of an *Escherichia coli* produced precursor peptide. Biotechnology, vol. 11 (1993) 11:64-70.
Ray et al. Production of salmon calcitonin by direct expression of a glycine-extended precursor in *Escherichia coli*. Protein Expression and Purification, (2002) 26:249-259.
Nozer M. Mehta. Oral Delivery and Recombinant Production of Peptide Hormones, Part II: Recombinant Production of Therapeutic Peptides. Biopharm. International (2004) pp. 44-46.
Mansoor et al. Oral Delivery of Mono-PEGylated sCT (Lys18) in Rats: Regional Difference in Stability and Hypocalcemic Effect. Pharmaceutical Development and Technology. (2005) 10:389-396.
Prego et al. Chitosan—PEG nanocapsules as new carriers for oral peptide delivery. Effect of chitosan pegylation degree. Journal of Controlled Release (2006) 111:299-308.
Garcia-Fuentes et al. A comparative study of the potential of solid triglyceride nanostructures coated with chitosan or poly(ethylene glycol) as carriers for oral calcitonin delivery. European Journal of Pharmaceutical Sciences (2005) 25:133-143.
Garcia-Fuentes et al. New surface-modified lipid nanoparticles as delivery vehicles for salmon calcitonin. International Journal of Pharmaceutics 296 (2005) 122-132.
Guggi et al. Systemic peptide delivery via the stomach: in vivo evaluation of an oral dosage form for salmon calcitonin. Journal of Controlled Release (2003) 92:125-135.
Guggi et al. In Vivo Evaluation of an Oral Salmon Calcitonin-Delivery System Based on a Thiolated Chitosan Carrier Matrix. Pharmaceutical Research. (2003) 20:1989-1994.
Dogru et al. Oral multiple w/o/w emulsion formulation of a peptide salmon calcitonin: in vitro-in vivo evaluation. Journal of Clinical Pharmacy and Therapeutics (2000) 25:435-443.
Sinko et al. Biopharmaceutical approaches for developing and assessing oral peptide delivery strategies and systems: in vitro permeability and in vivo oral absorption of salmon calcitonin (sCT). Pharmaceutical Research. (1999) 16:527-33.
Song et al. Enhanced intestinal absorption of salmon calcitonin (sCT) from proliposomes containing bile salts. Journal of Controlled Release. (2005) 106:298-308.
De la Fuente et al. Enhanced intestinal absorption of salmon calcitonin (sCT) from proliposomes containing bile salts. Nanomedicine, 2008, 3:845-857.
Caliceti et al. Development and in vivo evaluation of an oral insulin-PEG delivery system. European Journal of Pharmaceutical Sciences. (2004) 22:315-323.
Bernkop-Schnurch et al. The use of thiolated polymers as carrier matrix in oral peptide delivery—Proof of concept. Journal of Controlled Release (2005) 106:26-33.
Shen et al. Intestinal Patches for Oral Drug Delivery. Pharmaceutical Research. (2002) 10:391-395.

\* cited by examiner

| pIC50 | UGP302 | KBP-011 | KBP-023 | KBP-056 | KBP-088 |
|---|---|---|---|---|---|
| CTR | 8,49 | 7,90 | 8,29 | 8,31 | 8,49 |
| AMY-R | 8,69 | 8,15 | 8,50 | 8,53 | 8,76 |

SEQUENCE LISTING

```
<160> NUMBER OF SEQ ID NOS: 80

<210> SEQ ID NO 1
<211> LENGTH: 32
<212> TYPE: PRT
<213> ORGANISM: Artificial Sequence
<220> FEATURE:
<223> OTHER INFORMATION: calcitonin
<220> FEATURE:
<221> NAME/KEY: MOD_RES
<222> LOCATION: 32
<223> OTHER INFORMATION: C-terminal Pro is amidated

<400> SEQUENCE: 1

Cys Ser Asn Leu Ser Thr Cys Val Leu Gly Lys Leu Ser Gln Glu Leu
1               5                   10                  15

His Lys Leu Gln Thr Tyr Pro Arg Thr Asn Thr Gly Ser Gly Thr Pro
            20                  25                  30

<210> SEQ ID NO 2
<211> LENGTH: 32
<212> TYPE: PRT
<213> ORGANISM: Artificial Sequence
<220> FEATURE:
<223> OTHER INFORMATION: Calcitonin
<220> FEATURE:
<221> NAME/KEY: MOD_RES
<222> LOCATION: 32
<223> OTHER INFORMATION: C-terminal Pro is amidated

<400> SEQUENCE: 2

Cys Ser Asn Leu Ser Thr Cys Val Leu Gly Lys Leu Ser Gln Glu Leu
1               5                   10                  15
```

His Lys Leu Gln Thr Tyr Pro Arg Thr Asp Val Gly Ala Gly Thr Pro
            20                  25                  30

<210> SEQ ID NO 3
<211> LENGTH: 32
<212> TYPE: PRT
<213> ORGANISM: Artificial Sequence
<220> FEATURE:
<223> OTHER INFORMATION: Calcitonin
<220> FEATURE:
<221> NAME/KEY: MOD_RES
<222> LOCATION: 32
<223> OTHER INFORMATION: C-terminal Pro is amidated

<400> SEQUENCE: 3

Cys Ala Ser Leu Ser Thr Cys Val Leu Gly Lys Leu Ser Gln Glu Leu
1               5                   10                  15

His Lys Leu Gln Thr Tyr Pro Arg Thr Asp Val Gly Ala Gly Thr Pro
            20                  25                  30

<210> SEQ ID NO 4
<211> LENGTH: 32
<212> TYPE: PRT
<213> ORGANISM: Artificial Sequence
<220> FEATURE:
<223> OTHER INFORMATION: Calcitonin mimetic
<220> FEATURE:
<221> NAME/KEY: MOD_RES
<222> LOCATION: 1
<223> OTHER INFORMATION: N-terminal Cys is acetylated
<220> FEATURE:
<221> NAME/KEY: MOD_RES
<222> LOCATION: 32
<223> OTHER INFORMATION: C-terminal Pro is amidated

<400> SEQUENCE: 4

Cys Ser Asn Leu Ser Thr Cys Val Leu Gly Lys Leu Ser Gln Glu Leu
1               5                   10                  15

His Lys Leu Gln Thr Tyr Pro Arg Thr Asp Val Gly Ala Asn Ala Pro
            20                  25                  30

<210> SEQ ID NO 5
<211> LENGTH: 32
<212> TYPE: PRT
<213> ORGANISM: Artificial Sequence
<220> FEATURE:
<223> OTHER INFORMATION: Calcitonin mimetic
<220> FEATURE:
<221> NAME/KEY: SITE
<222> LOCATION: 15
<223> OTHER INFORMATION: Xaa is Asp or Glu
<220> FEATURE:
<221> NAME/KEY: SITE
<222> LOCATION: 22
<223> OTHER INFORMATION: Xaa is Phe or Tyr

<400> SEQUENCE: 5

Cys Ala Ser Leu Ser Thr Cys Val Leu Gly Arg Leu Ser Gln Xaa Leu
1               5                   10                  15

His Arg Leu Gln Thr Xaa Pro Arg Thr Asp Val Gly Ala Asn Ala Pro
            20                  25                  30

<210> SEQ ID NO 6
<211> LENGTH: 32
<212> TYPE: PRT
<213> ORGANISM: Artificial Sequence
<220> FEATURE:
<223> OTHER INFORMATION: Calcitonin mimetic
<220> FEATURE:

```
<221> NAME/KEY: SITE
<222> LOCATION: 15
<223> OTHER INFORMATION: Xaa is Asp or Glu
<220> FEATURE:
<221> NAME/KEY: SITE
<222> LOCATION: 22
<223> OTHER INFORMATION: Xaa is Phe or Tyr

<400> SEQUENCE: 6

Cys Ala Ser Leu Ser Thr Cys Met Leu Gly Lys Leu Thr Gln Xaa Leu
1               5                   10                  15

His Lys Leu Gln Thr Xaa Pro Arg Thr Asp Val Gly Ala Asn Ala Pro
            20                  25                  30

<210> SEQ ID NO 7
<211> LENGTH: 32
<212> TYPE: PRT
<213> ORGANISM: Artificial Sequence
<220> FEATURE:
<223> OTHER INFORMATION: Calcitonin mimetic
<220> FEATURE:
<221> NAME/KEY: SITE
<222> LOCATION: 15
<223> OTHER INFORMATION: Xaa is Asp or Glu
<220> FEATURE:
<221> NAME/KEY: SITE
<222> LOCATION: 22
<223> OTHER INFORMATION: Xaa is Phe or Tyr

<400> SEQUENCE: 7

Cys Ala Ser Leu Ser Thr Cys Val Leu Gly Lys Leu Ser Gln Xaa Leu
1               5                   10                  15

His Lys Leu Gln Thr Xaa Pro Lys Thr Asp Val Gly Ala Asn Ala Pro
            20                  25                  30

<210> SEQ ID NO 8
<211> LENGTH: 32
<212> TYPE: PRT
<213> ORGANISM: Artificial Sequence
<220> FEATURE:
<223> OTHER INFORMATION: Calcitonin mimetic
<220> FEATURE:
<221> NAME/KEY: SITE
<222> LOCATION: 15
<223> OTHER INFORMATION: Xaa is Asp or Glu
<220> FEATURE:
<221> NAME/KEY: SITE
<222> LOCATION: 22
<223> OTHER INFORMATION: Xaa is Phe or Tyr

<400> SEQUENCE: 8

Cys Ser Asn Leu Ser Thr Cys Met Leu Gly Arg Leu Ser Gln Xaa Leu
1               5                   10                  15

His Arg Leu Gln Thr Xaa Pro Lys Thr Asp Val Gly Ala Asn Ala Pro
            20                  25                  30

<210> SEQ ID NO 9
<211> LENGTH: 32
<212> TYPE: PRT
<213> ORGANISM: Artificial Sequence
<220> FEATURE:
<223> OTHER INFORMATION: Calcitonin mimetic
<220> FEATURE:
<221> NAME/KEY: MOD_RES
<222> LOCATION: 1
<223> OTHER INFORMATION: N-terminal Cys is acetylated
<220> FEATURE:
<221> NAME/KEY: MOD_RES
<222> LOCATION: 32
<223> OTHER INFORMATION: C-terminal Pro is amidated
```

<400> SEQUENCE: 9

Cys Ala Ser Leu Ser Thr Cys Val Leu Gly Arg Leu Ser Gln Glu Leu
1               5                   10                  15

His Arg Leu Gln Thr Phe Pro Arg Thr Asp Val Gly Ala Asn Ala Pro
            20                  25                  30

<210> SEQ ID NO 10
<211> LENGTH: 32
<212> TYPE: PRT
<213> ORGANISM: Artificial Sequence
<220> FEATURE:
<223> OTHER INFORMATION: Calcitonin mimetic
<220> FEATURE:
<221> NAME/KEY: MOD_RES
<222> LOCATION: 1
<223> OTHER INFORMATION: N-terminal Cys is acetylated
<220> FEATURE:
<221> NAME/KEY: MOD_RES
<222> LOCATION: 32
<223> OTHER INFORMATION: C-terminal Pro is amidated

<400> SEQUENCE: 10

Cys Ala Ser Leu Ser Thr Cys Met Leu Gly Lys Leu Thr Gln Glu Leu
1               5                   10                  15

His Lys Leu Gln Thr Phe Pro Arg Thr Asp Val Gly Ala Asn Ala Pro
            20                  25                  30

<210> SEQ ID NO 11
<211> LENGTH: 32
<212> TYPE: PRT
<213> ORGANISM: Artificial Sequence
<220> FEATURE:
<223> OTHER INFORMATION: Calcitonin mimetic
<220> FEATURE:
<221> NAME/KEY: MOD_RES
<222> LOCATION: 1
<223> OTHER INFORMATION: N-terminal Cys is acetylated
<220> FEATURE:
<221> NAME/KEY: MOD_RES
<222> LOCATION: 32
<223> OTHER INFORMATION: C-terminal Pro is amidated

<400> SEQUENCE: 11

Cys Ala Ser Leu Ser Thr Cys Val Leu Gly Lys Leu Ser Gln Asp Leu
1               5                   10                  15

His Lys Leu Gln Thr Phe Pro Lys Thr Asp Val Gly Ala Asn Ala Pro
            20                  25                  30

<210> SEQ ID NO 12
<211> LENGTH: 32
<212> TYPE: PRT
<213> ORGANISM: Artificial Sequence
<220> FEATURE:
<223> OTHER INFORMATION: Calcitonin mimetic
<220> FEATURE:
<221> NAME/KEY: MOD_RES
<222> LOCATION: 1
<223> OTHER INFORMATION: N-terminal Cys is acetylated
<220> FEATURE:
<221> NAME/KEY: MOD_RES
<222> LOCATION: 32
<223> OTHER INFORMATION: C-terminal Pro is amidated

<400> SEQUENCE: 12

Cys Ser Asn Leu Ser Thr Cys Met Leu Gly Arg Leu Ser Gln Glu Leu
1               5                   10                  15

His Arg Leu Gln Thr Phe Pro Lys Thr Asp Val Gly Ala Asn Ala Pro

```
                     20                   25                   30

<210> SEQ ID NO 13
<211> LENGTH: 32
<212> TYPE: PRT
<213> ORGANISM: Artificial sequence
<220> FEATURE:
<223> OTHER INFORMATION: Calcitonin
<220> FEATURE:
<221> NAME/KEY: MOD_RES
<222> LOCATION: 32
<223> OTHER INFORMATION: Amidation

<400> SEQUENCE: 13

Cys Gly Asn Leu Ser Thr Cys Met Leu Gly Thr Tyr Thr Gln Asp Leu
1               5                  10                  15

Asn Lys Phe His Thr Phe Pro Gln Thr Ser Ile Gly Val Glu Ala Pro
            20                  25                  30

<210> SEQ ID NO 14
<211> LENGTH: 32
<212> TYPE: PRT
<213> ORGANISM: Artificial Sequence
<220> FEATURE:
<223> OTHER INFORMATION: Calcitonin
<220> FEATURE:
<221> NAME/KEY: MOD_RES
<222> LOCATION: 32
<223> OTHER INFORMATION: C-terminal Pro is amidated

<400> SEQUENCE: 14

Cys Gly Asn Leu Ser Thr Cys Met Leu Gly Thr Tyr Thr Gln Asp Leu
1               5                  10                  15

Asn Lys Phe His Thr Phe Pro Gln Thr Ser Ile Gly Val Gly Ala Pro
            20                  25                  30

<210> SEQ ID NO 15
<211> LENGTH: 32
<212> TYPE: PRT
<213> ORGANISM: Artificial Sequence
<220> FEATURE:
<223> OTHER INFORMATION: Calcitonin
<220> FEATURE:
<221> NAME/KEY: MOD_RES
<222> LOCATION: 32
<223> OTHER INFORMATION: C-terminal Pro is amidated

<400> SEQUENCE: 15

Cys Ser Asn Leu Ser Thr Cys Val Leu Gly Thr Tyr Thr Gln Asp Leu
1               5                  10                  15

Asn Lys Phe His Thr Phe Pro Gln Thr Ala Ile Gly Val Gly Ala Pro
            20                  25                  30

<210> SEQ ID NO 16
<211> LENGTH: 32
<212> TYPE: PRT
<213> ORGANISM: Artificial Sequence
<220> FEATURE:
<223> OTHER INFORMATION: Calcitonin variant 1
<220> FEATURE:
<221> NAME/KEY: MOD_RES
<222> LOCATION: 32
<223> OTHER INFORMATION: C-terminal Pro is amidated

<400> SEQUENCE: 16

Cys Ser Asn Leu Ser Thr Cys Val Leu Gly Thr Tyr Ser Lys Asp Leu
1               5                  10                  15
```

Asn Asn Phe His Thr Phe Ser Gly Ile Gly Phe Gly Ala Glu Thr Pro
            20                  25                  30

<210> SEQ ID NO 17
<211> LENGTH: 32
<212> TYPE: PRT
<213> ORGANISM: Artificial Sequence
<220> FEATURE:
<223> OTHER INFORMATION: Variant 2
<220> FEATURE:
<221> NAME/KEY: MOD_RES
<222> LOCATION: 32
<223> OTHER INFORMATION: C-terminal Pro is amidated

<400> SEQUENCE: 17

Cys Ser Asn Leu Ser Thr Cys Val Leu Gly Thr Tyr Thr Gln Asp Leu
1               5                   10                  15

Asn Lys Phe His Thr Phe Pro Gln Thr Ala Ile Gly Val Gly Ala Pro
            20                  25                  30

<210> SEQ ID NO 18
<211> LENGTH: 32
<212> TYPE: PRT
<213> ORGANISM: Artificial Sequence
<220> FEATURE:
<223> OTHER INFORMATION: Calcitonin
<220> FEATURE:
<221> NAME/KEY: MOD_RES
<222> LOCATION: 32
<223> OTHER INFORMATION: C-terminal Pro is amidated

<400> SEQUENCE: 18

Cys Ser Asn Leu Ser Thr Cys Val Leu Ser Ala Tyr Trp Arg Asn Leu
1               5                   10                  15

Asn Asn Phe His Arg Phe Ser Gly Met Gly Phe Gly Pro Glu Thr Pro
            20                  25                  30

<210> SEQ ID NO 19
<211> LENGTH: 32
<212> TYPE: PRT
<213> ORGANISM: Artificial Sequence
<220> FEATURE:
<223> OTHER INFORMATION: Calcitonin
<220> FEATURE:
<221> NAME/KEY: MOD_RES
<222> LOCATION: 32
<223> OTHER INFORMATION: C-terminal Pro is amidated

<400> SEQUENCE: 19

Cys Gly Asn Leu Ser Thr Cys Met Leu Gly Thr Tyr Thr Gln Asp Phe
1               5                   10                  15

Asn Lys Phe His Thr Phe Pro Gln Thr Ala Ile Gly Val Gly Ala Pro
            20                  25                  30

<210> SEQ ID NO 20
<211> LENGTH: 32
<212> TYPE: PRT
<213> ORGANISM: Artificial Sequence
<220> FEATURE:
<223> OTHER INFORMATION: Calcitonin mimetic

<400> SEQUENCE: 20

Cys Ala Ser Leu Ser Thr Cys Val Leu Gly Arg Leu Ser Gln Glu Leu
1               5                   10                  15

His Arg Leu Gln Thr Phe Pro Lys Thr Asp Val Gly Ala Asn Ala Tyr
            20                  25                  30

<210> SEQ ID NO 21
<211> LENGTH: 32
<212> TYPE: PRT
<213> ORGANISM: Artificial Sequence
<220> FEATURE:
<223> OTHER INFORMATION: Calcitonin mimetic

<400> SEQUENCE: 21

Cys Ala Ser Leu Ser Thr Cys Met Leu Gly Lys Leu Thr Gln Glu Leu
1               5                   10                  15

His Lys Leu Gln Thr Phe Pro Lys Thr Asp Val Gly Ala Asn Ala Tyr
            20                  25                  30

<210> SEQ ID NO 22
<211> LENGTH: 32
<212> TYPE: PRT
<213> ORGANISM: Artificial Sequence
<220> FEATURE:
<223> OTHER INFORMATION: Calcitonin mimetic

<400> SEQUENCE: 22

Cys Ala Ser Leu Ser Thr Cys Val Leu Gly Lys Leu Ser Gln Asp Leu
1               5                   10                  15

His Lys Leu Gln Thr Phe Pro Lys Thr Asp Val Gly Ala Asn Ala Tyr
            20                  25                  30

<210> SEQ ID NO 23
<211> LENGTH: 32
<212> TYPE: PRT
<213> ORGANISM: Artificial Sequence
<220> FEATURE:
<223> OTHER INFORMATION: Calcitonin mimetic

<400> SEQUENCE: 23

Cys Ser Asn Leu Ser Thr Cys Met Leu Gly Arg Leu Ser Gln Glu Leu
1               5                   10                  15

His Arg Leu Gln Thr Phe Pro Lys Thr Asp Val Gly Ala Asn Ala Tyr
            20                  25                  30

<210> SEQ ID NO 24
<211> LENGTH: 32
<212> TYPE: PRT
<213> ORGANISM: Artificial Sequence
<220> FEATURE:
<223> OTHER INFORMATION: Calcitonin mimetic

<400> SEQUENCE: 24

Cys Ala Ser Leu Ser Thr Cys Val Leu Gly Arg Leu Ser Gln Glu Leu
1               5                   10                  15

His Arg Leu Gln Thr Phe Pro Arg Thr Asp Val Gly Ala Asn Ala Tyr
            20                  25                  30

<210> SEQ ID NO 25
<211> LENGTH: 32
<212> TYPE: PRT
<213> ORGANISM: Artificial Sequence
<220> FEATURE:
<223> OTHER INFORMATION: Calcitonin mimetic

<400> SEQUENCE: 25

Cys Ala Ser Leu Ser Thr Cys Met Leu Gly Lys Leu Thr Gln Glu Leu
1               5                   10                  15

His Lys Leu Gln Thr Phe Pro Arg Thr Asp Val Gly Ala Asn Ala Tyr
            20                  25                  30

```
<210> SEQ ID NO 26
<211> LENGTH: 32
<212> TYPE: PRT
<213> ORGANISM: Artificial Sequence
<220> FEATURE:
<223> OTHER INFORMATION: Calcitonin mimetic

<400> SEQUENCE: 26

Cys Ala Ser Leu Ser Thr Cys Val Leu Gly Arg Leu Ser Gln Glu Leu
1               5                   10                  15

His Arg Leu Gln Thr Phe Pro Lys Thr Asp Val Gly Ala Asn Ala Pro
            20                  25                  30

<210> SEQ ID NO 27
<211> LENGTH: 32
<212> TYPE: PRT
<213> ORGANISM: Artificial Sequence
<220> FEATURE:
<223> OTHER INFORMATION: Calcitonin mimetic

<400> SEQUENCE: 27

Cys Ala Ser Leu Ser Thr Cys Met Leu Gly Lys Leu Thr Gln Glu Leu
1               5                   10                  15

His Lys Leu Gln Thr Phe Pro Lys Thr Asp Val Gly Ala Asn Ala Pro
            20                  25                  30

<210> SEQ ID NO 28
<211> LENGTH: 32
<212> TYPE: PRT
<213> ORGANISM: Artificial Sequence
<220> FEATURE:
<223> OTHER INFORMATION: Calcitonin mimetic

<400> SEQUENCE: 28

Cys Ala Ser Leu Ser Thr Cys Val Leu Gly Arg Leu Ser Gln Glu Leu
1               5                   10                  15

His Arg Leu Gln Thr Phe Pro Arg Thr Asp Val Gly Ala Asn Ala Pro
            20                  25                  30

<210> SEQ ID NO 29
<211> LENGTH: 32
<212> TYPE: PRT
<213> ORGANISM: Artificial Sequence
<220> FEATURE:
<223> OTHER INFORMATION: calcitonin mimetic

<400> SEQUENCE: 29

Cys Ala Ser Leu Ser Thr Cys Met Leu Gly Lys Leu Thr Gln Glu Leu
1               5                   10                  15

His Lys Leu Gln Thr Phe Pro Arg Thr Asp Val Gly Ala Asn Ala Pro
            20                  25                  30

<210> SEQ ID NO 30
<211> LENGTH: 32
<212> TYPE: PRT
<213> ORGANISM: Artificial Sequence
<220> FEATURE:
<223> OTHER INFORMATION: calcitonin mimetic

<400> SEQUENCE: 30

Cys Ala Ser Leu Ser Thr Cys Val Leu Gly Lys Leu Ser Gln Glu Leu
1               5                   10                  15

His Lys Leu Gln Thr Phe Pro Lys Thr Asp Val Gly Ala Asn Ala Pro
```

<210> SEQ ID NO 31
<211> LENGTH: 32
<212> TYPE: PRT
<213> ORGANISM: Artificial Sequence
<220> FEATURE:
<223> OTHER INFORMATION: calcitonin mimetic

<400> SEQUENCE: 31

Cys Ser Asn Leu Ser Thr Cys Met Leu Gly Arg Leu Ser Gln Glu Leu
1               5                   10                  15
His Arg Leu Gln Thr Phe Pro Lys Thr Asp Val Gly Ala Asn Ala Pro
            20                  25                  30

<210> SEQ ID NO 32
<211> LENGTH: 32
<212> TYPE: PRT
<213> ORGANISM: Artificial Sequence
<220> FEATURE:
<223> OTHER INFORMATION: calcitonin mimetic

<400> SEQUENCE: 32

Cys Ala Ser Leu Ser Thr Cys Val Leu Gly Arg Leu Ser Gln Glu Leu
1               5                   10                  15
His Arg Leu Gln Thr Tyr Pro Arg Thr Asp Val Gly Ala Asn Ala Pro
            20                  25                  30

<210> SEQ ID NO 33
<211> LENGTH: 32
<212> TYPE: PRT
<213> ORGANISM: Artificial Sequence
<220> FEATURE:
<223> OTHER INFORMATION: calcitonin mimetic

<400> SEQUENCE: 33

Cys Ala Ser Leu Ser Thr Cys Met Leu Gly Lys Leu Thr Gln Glu Leu
1               5                   10                  15
His Lys Leu Gln Thr Tyr Pro Arg Thr Asp Val Gly Ala Asn Ala Pro
            20                  25                  30

<210> SEQ ID NO 34
<211> LENGTH: 32
<212> TYPE: PRT
<213> ORGANISM: Artificial Sequence
<220> FEATURE:
<223> OTHER INFORMATION: calcitonin mimetic

<400> SEQUENCE: 34

Cys Ala Ser Leu Ser Thr Cys Val Leu Gly Lys Leu Ser Gln Glu Leu
1               5                   10                  15
His Lys Leu Gln Thr Tyr Pro Lys Thr Asp Val Gly Ala Asn Ala Pro
            20                  25                  30

<210> SEQ ID NO 35
<211> LENGTH: 32
<212> TYPE: PRT
<213> ORGANISM: Artificial Sequence
<220> FEATURE:
<223> OTHER INFORMATION: calcitonin mimetic

<400> SEQUENCE: 35

Cys Ser Asn Leu Ser Thr Cys Met Leu Gly Arg Leu Ser Gln Glu Leu
1               5                   10                  15

His Arg Leu Gln Thr Tyr Pro Lys Thr Asp Val Gly Ala Asn Ala Pro
            20                  25                  30

<210> SEQ ID NO 36
<211> LENGTH: 32
<212> TYPE: PRT
<213> ORGANISM: Artificial Sequence
<220> FEATURE:
<223> OTHER INFORMATION: calcitonin mimetic

<400> SEQUENCE: 36

Cys Ala Ser Leu Ser Thr Cys Val Leu Gly Arg Leu Ser Gln Asp Leu
1               5                   10                  15

His Arg Leu Gln Thr Phe Pro Arg Thr Asp Val Gly Ala Asn Ala Pro
            20                  25                  30

<210> SEQ ID NO 37
<211> LENGTH: 32
<212> TYPE: PRT
<213> ORGANISM: Artificial Sequence
<220> FEATURE:
<223> OTHER INFORMATION: calcitonin mimetic

<400> SEQUENCE: 37

Cys Ala Ser Leu Ser Thr Cys Met Leu Gly Lys Leu Thr Gln Asp Leu
1               5                   10                  15

His Lys Leu Gln Thr Phe Pro Arg Thr Asp Val Gly Ala Asn Ala Pro
            20                  25                  30

<210> SEQ ID NO 38
<211> LENGTH: 32
<212> TYPE: PRT
<213> ORGANISM: Artificial Sequence
<220> FEATURE:
<223> OTHER INFORMATION: calcitonin mimetic

<400> SEQUENCE: 38

Cys Ala Ser Leu Ser Thr Cys Val Leu Gly Lys Leu Ser Gln Asp Leu
1               5                   10                  15

His Lys Leu Gln Thr Phe Pro Lys Thr Asp Val Gly Ala Asn Ala Pro
            20                  25                  30

<210> SEQ ID NO 39
<211> LENGTH: 32
<212> TYPE: PRT
<213> ORGANISM: Artificial Sequence
<220> FEATURE:
<223> OTHER INFORMATION: calcitonin mimetic

<400> SEQUENCE: 39

Cys Ser Asn Leu Ser Thr Cys Met Leu Gly Arg Leu Ser Gln Asp Leu
1               5                   10                  15

His Arg Leu Gln Thr Phe Pro Lys Thr Asp Val Gly Ala Asn Ala Pro
            20                  25                  30

<210> SEQ ID NO 40
<211> LENGTH: 32
<212> TYPE: PRT
<213> ORGANISM: Artificial Sequence
<220> FEATURE:
<223> OTHER INFORMATION: calcitonin mimetic

<400> SEQUENCE: 40

Cys Ala Ser Leu Ser Thr Cys Val Leu Gly Arg Leu Ser Gln Asp Leu
1               5                   10                  15

His Arg Leu Gln Thr Tyr Pro Arg Thr Asp Val Gly Ala Asn Ala Pro
            20                  25                  30

<210> SEQ ID NO 41
<211> LENGTH: 32
<212> TYPE: PRT
<213> ORGANISM: Artificial Sequence
<220> FEATURE:
<223> OTHER INFORMATION: calcitonin mimetic

<400> SEQUENCE: 41

Cys Ala Ser Leu Ser Thr Cys Met Leu Gly Lys Leu Thr Gln Asp Leu
1               5                   10                  15

His Lys Leu Gln Thr Tyr Pro Arg Thr Asp Val Gly Ala Asn Ala Pro
            20                  25                  30

<210> SEQ ID NO 42
<211> LENGTH: 32
<212> TYPE: PRT
<213> ORGANISM: Artificial Sequence
<220> FEATURE:
<223> OTHER INFORMATION: calcitonin mimetic

<400> SEQUENCE: 42

Cys Ala Ser Leu Ser Thr Cys Val Leu Gly Lys Leu Ser Gln Asp Leu
1               5                   10                  15

His Lys Leu Gln Thr Tyr Pro Lys Thr Asp Val Gly Ala Asn Ala Pro
            20                  25                  30

<210> SEQ ID NO 43
<211> LENGTH: 32
<212> TYPE: PRT
<213> ORGANISM: Artificial Sequence
<220> FEATURE:
<223> OTHER INFORMATION: calcitonin mimetic

<400> SEQUENCE: 43

Cys Ser Asn Leu Ser Thr Cys Met Leu Gly Arg Leu Ser Gln Asp Leu
1               5                   10                  15

His Arg Leu Gln Thr Tyr Pro Lys Thr Asp Val Gly Ala Asn Ala Pro
            20                  25                  30

<210> SEQ ID NO 44
<211> LENGTH: 32
<212> TYPE: PRT
<213> ORGANISM: Artificial Sequence
<220> FEATURE:
<223> OTHER INFORMATION: calcitonin mimetic
<220> FEATURE:
<221> NAME/KEY: MOD_RES
<222> LOCATION: 1
<223> OTHER INFORMATION: N-terminal Cys is acetylated
<220> FEATURE:
<221> NAME/KEY: MOD_RES
<222> LOCATION: 32
<223> OTHER INFORMATION: C-terminal Pro is amidated

<400> SEQUENCE: 44

Cys Ser Asn Leu Ser Thr Cys Met Leu Gly Arg Leu Ser Gln Asp Leu
1               5                   10                  15

His Arg Leu Gln Thr Tyr Pro Lys Thr Asp Val Gly Ala Asn Ala Pro
            20                  25                  30

<210> SEQ ID NO 45
<211> LENGTH: 32

```
<212> TYPE: PRT
<213> ORGANISM: Artificial Sequence
<220> FEATURE:
<223> OTHER INFORMATION: calcitonin mimetic
<220> FEATURE:
<221> NAME/KEY: SITE
<222> LOCATION: 15
<223> OTHER INFORMATION: Xaa is Asp or Glu
<220> FEATURE:
<221> NAME/KEY: SITE
<222> LOCATION: 22
<223> OTHER INFORMATION: Xaa is Phe or Tyr

<400> SEQUENCE: 45

Cys Ala Ser Leu Ser Thr Cys Val Leu Gly Arg Leu Ser Gln Xaa Leu
1               5                   10                  15

His Arg Leu Gln Thr Xaa Pro Lys Thr Asp Val Gly Ala Asn Ala Tyr
            20                  25                  30

<210> SEQ ID NO 46
<211> LENGTH: 32
<212> TYPE: PRT
<213> ORGANISM: Artificial Sequence
<220> FEATURE:
<223> OTHER INFORMATION: calcitonin mimetic
<220> FEATURE:
<221> NAME/KEY: SITE
<222> LOCATION: 15
<223> OTHER INFORMATION: Xaa is Asp or Glu
<220> FEATURE:
<221> NAME/KEY: SITE
<222> LOCATION: 22
<223> OTHER INFORMATION: Xaa is Phe or Tyr

<400> SEQUENCE: 46

Cys Ala Ser Leu Ser Thr Cys Met Leu Gly Lys Leu Thr Gln Xaa Leu
1               5                   10                  15

His Lys Leu Gln Thr Xaa Pro Lys Thr Asp Val Gly Ala Asn Ala Tyr
            20                  25                  30

<210> SEQ ID NO 47
<211> LENGTH: 32
<212> TYPE: PRT
<213> ORGANISM: Artificial Sequence
<220> FEATURE:
<223> OTHER INFORMATION: calcitonin mimetic
<220> FEATURE:
<221> NAME/KEY: SITE
<222> LOCATION: 15
<223> OTHER INFORMATION: Xaa is Asp or Glu
<220> FEATURE:
<221> NAME/KEY: SITE
<222> LOCATION: 22
<223> OTHER INFORMATION: Xaa is Phe or Tyr

<400> SEQUENCE: 47

Cys Ala Ser Leu Ser Thr Cys Val Leu Gly Lys Leu Ser Gln Xaa Leu
1               5                   10                  15

His Lys Leu Gln Thr Xaa Pro Lys Thr Asp Val Gly Ala Asn Ala Tyr
            20                  25                  30

<210> SEQ ID NO 48
<211> LENGTH: 32
<212> TYPE: PRT
<213> ORGANISM: Artificial Sequence
<220> FEATURE:
<223> OTHER INFORMATION: calcitonin mimetic
<220> FEATURE:
<221> NAME/KEY: SITE
<222> LOCATION: 15
```

```
<223> OTHER INFORMATION: Xaa is Asp or Glu
<220> FEATURE:
<221> NAME/KEY: SITE
<222> LOCATION: 22
<223> OTHER INFORMATION: Xaa is Phe or Tyr

<400> SEQUENCE: 48

Cys Ser Asn Leu Ser Thr Cys Met Leu Gly Arg Leu Ser Gln Xaa Leu
1               5                   10                  15

His Arg Leu Gln Thr Xaa Pro Lys Thr Asp Val Gly Ala Asn Ala Tyr
            20                  25                  30

<210> SEQ ID NO 49
<211> LENGTH: 32
<212> TYPE: PRT
<213> ORGANISM: Artificial Sequence
<220> FEATURE:
<223> OTHER INFORMATION: calcitonin mimetic
<220> FEATURE:
<221> NAME/KEY: SITE
<222> LOCATION: 15
<223> OTHER INFORMATION: Xaa is Asp or Glu
<220> FEATURE:
<221> NAME/KEY: SITE
<222> LOCATION: 22
<223> OTHER INFORMATION: Xaa is Phe or Tyr

<400> SEQUENCE: 49

Cys Ala Ser Leu Ser Thr Cys Val Leu Gly Arg Leu Ser Gln Xaa Leu
1               5                   10                  15

His Arg Leu Gln Thr Xaa Pro Arg Thr Asp Val Gly Ala Asn Ala Tyr
            20                  25                  30

<210> SEQ ID NO 50
<211> LENGTH: 32
<212> TYPE: PRT
<213> ORGANISM: Artificial Sequence
<220> FEATURE:
<223> OTHER INFORMATION: calcitonin mimetic
<220> FEATURE:
<221> NAME/KEY: SITE
<222> LOCATION: 15
<223> OTHER INFORMATION: Xaa is Asp or Glu
<220> FEATURE:
<221> NAME/KEY: SITE
<222> LOCATION: 22
<223> OTHER INFORMATION: Xaa is Phe or Tyr

<400> SEQUENCE: 50

Cys Ala Ser Leu Ser Thr Cys Met Leu Gly Lys Leu Thr Gln Xaa Leu
1               5                   10                  15

His Lys Leu Gln Thr Xaa Pro Arg Thr Asp Val Gly Ala Asn Ala Tyr
            20                  25                  30

<210> SEQ ID NO 51
<211> LENGTH: 32
<212> TYPE: PRT
<213> ORGANISM: Artificial Sequence
<220> FEATURE:
<223> OTHER INFORMATION: calcitonin mimetic
<220> FEATURE:
<221> NAME/KEY: SITE
<222> LOCATION: 15
<223> OTHER INFORMATION: Xaa is Asp or Glu
<220> FEATURE:
<221> NAME/KEY: SITE
<222> LOCATION: 22
<223> OTHER INFORMATION: Xaa is Phe or Tyr

<400> SEQUENCE: 51
```

Cys Ala Ser Leu Ser Thr Cys Val Leu Gly Arg Leu Ser Gln Xaa Leu
1               5                   10                  15

His Arg Leu Gln Thr Xaa Pro Lys Thr Asp Val Gly Ala Asn Ala Pro
            20                  25                  30

<210> SEQ ID NO 52
<211> LENGTH: 32
<212> TYPE: PRT
<213> ORGANISM: Artificial Sequence
<220> FEATURE:
<223> OTHER INFORMATION: calcitonin mimetic
<220> FEATURE:
<221> NAME/KEY: SITE
<222> LOCATION: 15
<223> OTHER INFORMATION: Xaa is Asp or Glu
<220> FEATURE:
<221> NAME/KEY: SITE
<222> LOCATION: 22
<223> OTHER INFORMATION: Xaa is Phe or Tyr

<400> SEQUENCE: 52

Cys Ala Ser Leu Ser Thr Cys Met Leu Gly Lys Leu Thr Gln Xaa Leu
1               5                   10                  15

His Lys Leu Gln Thr Xaa Pro Lys Thr Asp Val Gly Ala Asn Ala Pro
            20                  25                  30

<210> SEQ ID NO 53
<211> LENGTH: 32
<212> TYPE: PRT
<213> ORGANISM: Artificial Sequence
<220> FEATURE:
<223> OTHER INFORMATION: Calcitonin mimetic
<220> FEATURE:
<221> NAME/KEY: SITE
<222> LOCATION: 8
<223> OTHER INFORMATION: Xaa is Val or Met
<220> FEATURE:
<221> NAME/KEY: SITE
<222> LOCATION: 11
<223> OTHER INFORMATION: Xaa is Lys or Arg
<220> FEATURE:
<221> NAME/KEY: SITE
<222> LOCATION: 15
<223> OTHER INFORMATION: Xaa is Asp or Glu
<220> FEATURE:
<221> NAME/KEY: SITE
<222> LOCATION: 18
<223> OTHER INFORMATION: Xaa is Lys or Arg
<220> FEATURE:
<221> NAME/KEY: SITE
<222> LOCATION: 21
<223> OTHER INFORMATION: Xaa is Ser or Thr
<220> FEATURE:
<221> NAME/KEY: SITE
<222> LOCATION: 22
<223> OTHER INFORMATION: Xaa is Phe or Tyr
<220> FEATURE:
<221> NAME/KEY: SITE
<222> LOCATION: 24
<223> OTHER INFORMATION: Xaa is Lys or Arg
<220> FEATURE:
<221> NAME/KEY: SITE
<222> LOCATION: 32
<223> OTHER INFORMATION: Xaa is Pro or Tyr

<400> SEQUENCE: 53

Cys Ala Ser Leu Ser Thr Cys Xaa Leu Gly Xaa Leu Ser Gln Xaa Leu
1               5                   10                  15

His Xaa Leu Gln Xaa Xaa Pro Xaa Thr Asp Val Gly Ala Asn Ala Xaa
            20                  25                  30

```
<210> SEQ ID NO 54
<211> LENGTH: 32
<212> TYPE: PRT
<213> ORGANISM: Artificial Sequence
<220> FEATURE:
<223> OTHER INFORMATION: Calcitonin mimetic
<220> FEATURE:
<221> NAME/KEY: SITE
<222> LOCATION: 15
<223> OTHER INFORMATION: Xaa is Asp or Glu
<220> FEATURE:
<221> NAME/KEY: SITE
<222> LOCATION: 22
<223> OTHER INFORMATION: Xaa is Phe or Tyr

<400> SEQUENCE: 54

Cys Ala Ser Leu Ser Thr Cys Met Leu Gly Arg Leu Ser Gln Xaa Leu
1               5                   10                  15

His Arg Leu Gln Thr Xaa Pro Lys Thr Asp Val Gly Ala Asn Ala Pro
            20                  25                  30

<210> SEQ ID NO 55
<211> LENGTH: 32
<212> TYPE: PRT
<213> ORGANISM: Artificial Sequence
<220> FEATURE:
<223> OTHER INFORMATION: Calcitonin mimetic
<220> FEATURE:
<221> NAME/KEY: SITE
<222> LOCATION: 15
<223> OTHER INFORMATION: Xaa is Asp or Glu
<220> FEATURE:
<221> NAME/KEY: SITE
<222> LOCATION: 22
<223> OTHER INFORMATION: Xaa is Phe or Tyr

<400> SEQUENCE: 55

Cys Ala Ser Leu Ser Thr Cys Met Leu Gly Lys Leu Thr Gln Xaa Leu
1               5                   10                  15

His Lys Leu Gln Thr Xaa Pro Lys Thr Asp Val Gly Ala Asn Ala Pro
            20                  25                  30

<210> SEQ ID NO 56
<211> LENGTH: 32
<212> TYPE: PRT
<213> ORGANISM: Artificial Sequence
<220> FEATURE:
<223> OTHER INFORMATION: Calcitonin mimetic
<220> FEATURE:
<221> NAME/KEY: SITE
<222> LOCATION: 15
<223> OTHER INFORMATION: Xaa is Asp or Glu
<220> FEATURE:
<221> NAME/KEY: SITE
<222> LOCATION: 22
<223> OTHER INFORMATION: Xaa is Phy or Tyr

<400> SEQUENCE: 56

Cys Ala Ser Leu Ser Thr Cys Val Leu Gly Lys Leu Ser Gln Xaa Leu
1               5                   10                  15

His Lys Leu Gln Thr Xaa Pro Arg Thr Asp Val Gly Ala Asn Ala Pro
            20                  25                  30

<210> SEQ ID NO 57
<211> LENGTH: 32
<212> TYPE: PRT
<213> ORGANISM: Artificial Sequence
<220> FEATURE:
<223> OTHER INFORMATION: Calcitonin mimetic
```

```
<220> FEATURE:
<221> NAME/KEY: SITE
<222> LOCATION: 15
<223> OTHER INFORMATION: Xaa is Asp or Glu
<220> FEATURE:
<221> NAME/KEY: SITE
<222> LOCATION: 22
<223> OTHER INFORMATION: Xaa is Phe or Tyr

<400> SEQUENCE: 57

Cys Ser Asn Leu Ser Thr Cys Val Leu Gly Arg Leu Ser Gln Xaa Leu
1               5                   10                  15

His Arg Leu Gln Thr Xaa Pro Lys Thr Asp Val Gly Ala Asn Ala Pro
            20                  25                  30

<210> SEQ ID NO 58
<211> LENGTH: 32
<212> TYPE: PRT
<213> ORGANISM: Artificial Sequence
<220> FEATURE:
<223> OTHER INFORMATION: Calcitonin mimetic
<220> FEATURE:
<221> NAME/KEY: SITE
<222> LOCATION: 15
<223> OTHER INFORMATION: Xaa is Asp or Glu
<220> FEATURE:
<221> NAME/KEY: SITE
<222> LOCATION: 22
<223> OTHER INFORMATION: Xaa is Phe or Tyr

<400> SEQUENCE: 58

Cys Ala Ser Leu Ser Thr Cys Val Leu Gly Lys Leu Ser Gln Xaa Leu
1               5                   10                  15

His Lys Leu Gln Ser Xaa Pro Lys Thr Asp Val Gly Ala Asn Ala Pro
            20                  25                  30

<210> SEQ ID NO 59
<211> LENGTH: 32
<212> TYPE: PRT
<213> ORGANISM: Artificial Sequence
<220> FEATURE:
<223> OTHER INFORMATION: Calcitonin mimetic
<220> FEATURE:
<221> NAME/KEY: SITE
<222> LOCATION: 15
<223> OTHER INFORMATION: Xaa is Asp or Glu
<220> FEATURE:
<221> NAME/KEY: SITE
<222> LOCATION: 22
<223> OTHER INFORMATION: Xaa is Phe or Tyr

<400> SEQUENCE: 59

Cys Ala Ser Leu Ser Thr Cys Val Leu Gly Lys Leu Ser Gln Xaa Leu
1               5                   10                  15

His Lys Leu Gln Thr Xaa Pro Lys Thr Asp Val Gly Ala Asn Ala Pro
            20                  25                  30

<210> SEQ ID NO 60
<211> LENGTH: 32
<212> TYPE: PRT
<213> ORGANISM: Artificial Sequence
<220> FEATURE:
<223> OTHER INFORMATION: Calcitonin mimetic

<400> SEQUENCE: 60

Cys Ala Ser Leu Ser Thr Cys Val Leu Gly Arg Leu Ser Gln Glu Leu
1               5                   10                  15

His Arg Leu Gln Ser Phe Pro Arg Thr Asp Val Gly Ala Asn Ala Pro
```

<210> SEQ ID NO 61
<211> LENGTH: 32
<212> TYPE: PRT
<213> ORGANISM: Artificial Sequence
<220> FEATURE:
<223> OTHER INFORMATION: Calcitonin mimetic

<400> SEQUENCE: 61

Cys Ala Ser Leu Ser Thr Cys Met Leu Gly Lys Leu Thr Gln Glu Leu
1               5                   10                  15

His Lys Leu Gln Ser Phe Pro Arg Thr Asp Val Gly Ala Asn Ala Pro
            20                  25                  30

<210> SEQ ID NO 62
<211> LENGTH: 32
<212> TYPE: PRT
<213> ORGANISM: Artificial Sequence
<220> FEATURE:
<223> OTHER INFORMATION: Calcitonin mimetic

<400> SEQUENCE: 62

Cys Ala Ser Leu Ser Thr Cys Val Leu Gly Lys Leu Ser Gln Glu Leu
1               5                   10                  15

His Lys Leu Gln Ser Phe Pro Lys Thr Asp Val Gly Ala Asn Ala Pro
            20                  25                  30

<210> SEQ ID NO 63
<211> LENGTH: 32
<212> TYPE: PRT
<213> ORGANISM: Artificial Sequence
<220> FEATURE:
<223> OTHER INFORMATION: Calcitonin mimetic

<400> SEQUENCE: 63

Cys Ser Asn Leu Ser Thr Cys Met Leu Gly Arg Leu Ser Gln Glu Leu
1               5                   10                  15

His Arg Leu Gln Ser Phe Pro Lys Thr Asp Val Gly Ala Asn Ala Pro
            20                  25                  30

<210> SEQ ID NO 64
<211> LENGTH: 32
<212> TYPE: PRT
<213> ORGANISM: Artificial Sequence
<220> FEATURE:
<223> OTHER INFORMATION: Calcitonin mimetic

<400> SEQUENCE: 64

Cys Ala Ser Leu Ser Thr Cys Val Leu Gly Arg Leu Ser Gln Glu Leu
1               5                   10                  15

His Arg Leu Gln Ser Tyr Pro Arg Thr Asp Val Gly Ala Asn Ala Pro
            20                  25                  30

<210> SEQ ID NO 65
<211> LENGTH: 32
<212> TYPE: PRT
<213> ORGANISM: Artificial Sequence
<220> FEATURE:
<223> OTHER INFORMATION: Calcitonin mimetic

<400> SEQUENCE: 65

Cys Ala Ser Leu Ser Thr Cys Met Leu Gly Lys Leu Thr Gln Glu Leu
1               5                   10                  15

His Lys Leu Gln Ser Tyr Pro Arg Thr Asp Val Gly Ala Asn Ala Pro
            20                  25                  30

<210> SEQ ID NO 66
<211> LENGTH: 32
<212> TYPE: PRT
<213> ORGANISM: Artificial Sequence
<220> FEATURE:
<223> OTHER INFORMATION: Calcitonin mimetic

<400> SEQUENCE: 66

Cys Ala Ser Leu Ser Thr Cys Val Leu Gly Lys Leu Ser Gln Glu Leu
1               5                   10                  15

His Lys Leu Gln Ser Tyr Pro Lys Thr Asp Val Gly Ala Asn Ala Pro
            20                  25                  30

<210> SEQ ID NO 67
<211> LENGTH: 32
<212> TYPE: PRT
<213> ORGANISM: Artificial Sequence
<220> FEATURE:
<223> OTHER INFORMATION: Calcitonin mimetics

<400> SEQUENCE: 67

Cys Ser Asn Leu Ser Thr Cys Met Leu Gly Arg Leu Ser Gln Glu Leu
1               5                   10                  15

His Arg Leu Gln Ser Tyr Pro Lys Thr Asp Val Gly Ala Asn Ala Pro
            20                  25                  30

<210> SEQ ID NO 68
<211> LENGTH: 32
<212> TYPE: PRT
<213> ORGANISM: Artificial Sequence
<220> FEATURE:
<223> OTHER INFORMATION: Calcitonin mimetic

<400> SEQUENCE: 68

Cys Ala Ser Leu Ser Thr Cys Val Leu Gly Arg Leu Ser Gln Asp Leu
1               5                   10                  15

His Arg Leu Gln Ser Phe Pro Arg Thr Asp Val Gly Ala Asn Ala Pro
            20                  25                  30

<210> SEQ ID NO 69
<211> LENGTH: 32
<212> TYPE: PRT
<213> ORGANISM: Artificial Sequence
<220> FEATURE:
<223> OTHER INFORMATION: Calcitonin mimetic

<400> SEQUENCE: 69

Cys Ala Ser Leu Ser Thr Cys Met Leu Gly Lys Leu Thr Gln Asp Leu
1               5                   10                  15

His Lys Leu Gln Ser Phe Pro Arg Thr Asp Val Gly Ala Asn Ala Pro
            20                  25                  30

<210> SEQ ID NO 70
<211> LENGTH: 32
<212> TYPE: PRT
<213> ORGANISM: Artificial Sequence
<220> FEATURE:
<223> OTHER INFORMATION: Calcitonin mimetic

<400> SEQUENCE: 70

Cys Ala Ser Leu Ser Thr Cys Val Leu Gly Lys Leu Ser Gln Asp Leu
1               5                   10                  15

His Lys Leu Gln Ser Phe Pro Lys Thr Asp Val Gly Ala Asn Ala Pro
            20                  25                  30

<210> SEQ ID NO 71
<211> LENGTH: 32
<212> TYPE: PRT
<213> ORGANISM: Artificial Sequence
<220> FEATURE:
<223> OTHER INFORMATION: Calcitonin mimetic

<400> SEQUENCE: 71

Cys Ser Asn Leu Ser Thr Cys Met Leu Gly Arg Leu Ser Gln Asp Leu
1               5                   10                  15

His Arg Leu Gln Ser Phe Pro Lys Thr Asp Val Gly Ala Asn Ala Pro
            20                  25                  30

<210> SEQ ID NO 72
<211> LENGTH: 32
<212> TYPE: PRT
<213> ORGANISM: Artificial Sequence
<220> FEATURE:
<223> OTHER INFORMATION: Calcitonin mimetic

<400> SEQUENCE: 72

Cys Ala Ser Leu Ser Thr Cys Val Leu Gly Arg Leu Ser Gln Asp Leu
1               5                   10                  15

His Arg Leu Gln Ser Tyr Pro Arg Thr Asp Val Gly Ala Asn Ala Pro
            20                  25                  30

<210> SEQ ID NO 73
<211> LENGTH: 32
<212> TYPE: PRT
<213> ORGANISM: Artificial Sequence
<220> FEATURE:
<223> OTHER INFORMATION: Calcitonin mimetic

<400> SEQUENCE: 73

Cys Ala Ser Leu Ser Thr Cys Met Leu Gly Lys Leu Thr Gln Asp Leu
1               5                   10                  15

His Lys Leu Gln Ser Tyr Pro Arg Thr Asp Val Gly Ala Asn Ala Pro
            20                  25                  30

<210> SEQ ID NO 74
<211> LENGTH: 32
<212> TYPE: PRT
<213> ORGANISM: Artificial Sequence
<220> FEATURE:
<223> OTHER INFORMATION: Calcitonin mimetic

<400> SEQUENCE: 74

Cys Ala Ser Leu Ser Thr Cys Val Leu Gly Lys Leu Ser Gln Asp Leu
1               5                   10                  15

His Lys Leu Gln Ser Tyr Pro Lys Thr Asp Val Gly Ala Asn Ala Pro
            20                  25                  30

<210> SEQ ID NO 75
<211> LENGTH: 32
<212> TYPE: PRT
<213> ORGANISM: Artificial Sequence
<220> FEATURE:
<223> OTHER INFORMATION: Calcitonin mimetic

<400> SEQUENCE: 75

Cys Ser Asn Leu Ser Thr Cys Met Leu Gly Arg Leu Ser Gln Asp Leu

```
              1               5                  10                  15
His Arg Leu Gln Ser Tyr Pro Lys Thr Asp Val Gly Ala Asn Ala Pro
                20                  25                  30

<210> SEQ ID NO 76
<211> LENGTH: 32
<212> TYPE: PRT
<213> ORGANISM: Artificial Sequence
<220> FEATURE:
<223> OTHER INFORMATION: Calcitonin mimetic

<400> SEQUENCE: 76

Cys Ser Asn Leu Ser Thr Cys Val Leu Gly Lys Leu Ser Gln Glu Leu
1               5                  10                  15

His Lys Leu Gln Thr Tyr Pro Arg Thr Asp Val Gly Ala Asn Ala Pro
                20                  25                  30

<210> SEQ ID NO 77
<211> LENGTH: 32
<212> TYPE: PRT
<213> ORGANISM: Artificial Sequence
<220> FEATURE:
<223> OTHER INFORMATION: Calcitonin mimetic

<400> SEQUENCE: 77

Cys Ala Ser Leu Ser Thr Cys Met Leu Gly Arg Leu Ser Gln Asp Leu
1               5                  10                  15

His Arg Leu Gln Thr Tyr Pro Lys Thr Asp Val Gly Ala Asn Ala Pro
                20                  25                  30

<210> SEQ ID NO 78
<211> LENGTH: 32
<212> TYPE: PRT
<213> ORGANISM: Artificial Sequence
<220> FEATURE:
<223> OTHER INFORMATION: Calcitonin mimetic
<220> FEATURE:
<221> NAME/KEY: MOD_RES
<222> LOCATION: 1
<223> OTHER INFORMATION: N-terminal Cys is acetylated
<220> FEATURE:
<221> NAME/KEY: MOD_RES
<222> LOCATION: 32
<223> OTHER INFORMATION: C-terminal Pro is amidated

<400> SEQUENCE: 78

Cys Ala Ser Leu Ser Thr Cys Val Leu Gly Lys Leu Ser Gln Asp Leu
1               5                  10                  15

His Lys Leu Gln Ser Tyr Pro Lys Thr Asp Val Gly Ala Asn Ala Pro
                20                  25                  30

<210> SEQ ID NO 79
<211> LENGTH: 32
<212> TYPE: PRT
<213> ORGANISM: Artificial Sequence
<220> FEATURE:
<223> OTHER INFORMATION: Calcitonin mimetic
<220> FEATURE:
<221> NAME/KEY: MOD_RES
<222> LOCATION: 1
<223> OTHER INFORMATION: N-terminal Cys is acetylated
<220> FEATURE:
<221> NAME/KEY: MOD_RES
<222> LOCATION: 32
<223> OTHER INFORMATION: C-terminal Pro is amidated

<400> SEQUENCE: 79
```

```
Cys Ala Ser Leu Ser Thr Cys Val Leu Gly Lys Leu Ser Gln Glu Leu
1               5                   10                  15

His Lys Leu Gln Thr Phe Pro Lys Thr Asp Val Gly Ala Asn Ala Pro
            20                  25                  30

<210> SEQ ID NO 80
<211> LENGTH: 32
<212> TYPE: PRT
<213> ORGANISM: Artificial Sequence
<220> FEATURE:
<223> OTHER INFORMATION: Calcitonin mimetic
<220> FEATURE:
<221> NAME/KEY: MOD_RES
<222> LOCATION: 1
<223> OTHER INFORMATION: N-terminal Cys is acetylated
<220> FEATURE:
<221> NAME/KEY: MOD_RES
<222> LOCATION: 32
<223> OTHER INFORMATION: C-terminal Pro is amidated

<400> SEQUENCE: 80

Cys Ala Ser Leu Ser Thr Cys Val Leu Gly Lys Leu Ser Gln Asp Leu
1               5                   10                  15

His Lys Leu Gln Thr Tyr Pro Lys Thr Asp Val Gly Ala Asn Ala Pro
            20                  25                  30
```

CALCITONIN MIMETICS FOR TREATING DISEASES AND DISORDERS

The present invention relates to mimetics of calcitonin, and extends to their use as medicaments in the treatment of various diseases and disorders, including, but not limited to diabetes (Type I and Type II), excess bodyweight, excessive food consumption and metabolic syndrome, the regulation of blood glucose levels, the regulation of response to glucose tolerance tests, the regulation of food intake, the treatment of osteoporosis and the treatment of osteoarthritis.

Worldwide, there are about 250 million diabetics and the number is projected to double in the next two decades. Over 90% of this population suffers from type 2 diabetes mellitus (T2DM). It is estimated that only 50-60% of persons affected with T2DM or in stages preceding overt T2DM are currently diagnosed.

T2DM is a heterogeneous disease characterized by abnormalities in carbohydrate and fat metabolism. The causes of T2DM are multi-factorial and include both genetic and environmental elements that affect β-cell function and insulin sensitivity in tissues such as muscle, liver, pancreas and adipose tissue. As a consequence impaired insulin secretion is observed and paralleled by a progressive decline in β-cell function and chronic insulin resistance. The inability of the endocrine pancreas to compensate for peripheral insulin resistance leads to hyperglycaemia and onset of clinical diabetes. Tissue resistance to insulin-mediated glucose uptake is now recognized as a major pathophysiologic determinant of T2DM.

A success criterion for an optimal T2DM intervention is the lowering of blood glucose levels, which can be both chronic lowering of blood glucose levels and increased ability to tolerate high glucose levels after food intake, described by lower peak glucose levels and faster clearance. Both of these situations exert less strain on β-cell insulin output and function.

Type I diabetes is characterised by a loss of the ability to produce insulin in response to food intake and hence an inability to regulate blood glucose to a normal physiological level.

The physical structure of bone may be compromised by a variety of factors, including disease and injury. One of the most common bone diseases is osteoporosis, which is characterized by low bone mass and structural deterioration of bone tissue, leading to bone fragility and an increased susceptibility to fractures, particularly of the hip, spine and wrist. Osteoporosis develops when there is an imbalance such that the rate of bone resorption exceeds the rate of bone formation. Administering an effective amount of an anti-resorptive agent, such as calcitonin, has shown to prevent resorption of bone.

Inflammatory or degenerative diseases, including diseases of the joints, e.g. osteoarthritis (OA), rheumatoid arthritis (RA) or juvenile rheumatoid arthritis (JRA), and including inflammation that results from autoimmune response, e.g. lupus, ankylosing spondylitis (AS) or multiple sclerosis (MS), can lead to substantial loss of mobility due to pain and joint destruction. Cartilage that covers and cushions bone within joints may become degraded over time thus undesirably permitting direct contact of two bones that can limit motion of one bone relative to the other and/or cause damage to one by the other during motion of the joint. Subchondral bone just beneath the cartilage may also degrade.

Administering an effective amount of an anti-resorptive agent, such as calcitonin, may prevent resorption of bone.

WO2013/067357 discloses synthetic variants of natural calcitonins having modified amino acid sequences which are intended to provide improved properties.

Calcitonins are highly conserved over a wide range of species. Full-length native calcitonin is 32 amino acids in length. The sequences of examples of natural calcitonins are set out below (in each case the sequence has a C-terminal amidation—not shown):

| Salmon | CSNLSTCVLGKLSQELHKLQTYPRTNTGSGTP | SEQ ID NO: 1 |
|---|---|---|
| Eel | CSNLSTCVLGKLSQELHKLQTYPRTDVGAGTP | SEQ ID NO: 2 |
| Chicken | CASLSTCVLGKLSQELHKLQTYPRTDVGAGTP | SEQ ID NO: 3 |
| Mouse | CGNLSTCMLGTYTQDLNKFHTFPQTSIGVEAP | SEQ ID NO: 13 |
| Rat | CGNLSTCMLGTYTQDLNKFHTFPQTSIGVGAP | SEQ ID NO: 14 |
| Horse | CSNLSTCVLGTYTQDLNKFHTFPQTAIGVGAP | SEQ ID NO: 15 |
| Canine-1 | CSNLSTCVLGTYSKDLNNFHTFSGIGFGAETP | SEQ ID NO: 16 |
| Canine-2 | CSNLSTCVLGTYTQDLNKFHTFPQTAIGVGAP | SEQ ID NO: 17 |
| Porcine | CSNLSTCVLSAYWRNLNNFHRFSGMGFGPETP | SEQ ID NO: 18 |
| Human | CGNLSTCMLGTYTQDFNKFHTFPQTAIGVGAP | SEQ ID NO: 19 |

A comparison of the amino acid sequences of various natural calcitonins and UGP302 from WO2013/067357 is as follows:

TABLE 1

| Nano | 1 | 2 | 3 | 4 | 5 | 6 | 7 | 8 | 9 | 10 | 11 | 12 | 13 | 14 | 15 | 16 | 17 |
|---|---|---|---|---|---|---|---|---|---|---|---|---|---|---|---|---|---|
| Salmon Calcitonin[1] | C | S | N | L | S | T | C | V | L | G | K | L | S | Q | E | L | H |
| Eel Calcitonin[2] | C | S | N | L | S | T | C | V | L | G | K | L | S | Q | E | L | H |

TABLE 1-continued

|  | 1 | 2 | 3 | 4 | 5 | 6 | 7 | 8 | 9 | 10 | 11 | 12 | 13 | 14 | 15 | 16 | 17 |
|---|---|---|---|---|---|---|---|---|---|---|---|---|---|---|---|---|---|
| Chicken Calcitonin[3] | C | A | S | L | S | T | C | V | L | G | K | L | S | Q | E | L | H |
| UGP302[4] | AcC | S | N | L | S | T | C | V | L | G | K | L | S | Q | E | L | H |

|  | Nano | 18 | 19 | 20 | 21 | 22 | 25 | 24 | 25 | 26 | 27 | 28 | 29 | 30 | 31 | 32 |
|---|---|---|---|---|---|---|---|---|---|---|---|---|---|---|---|---|
| Salmon Calcitonin[1] |  | K | L | Q | T | Y | P | R | T | N | T | S | G | T | P—NH$_2$ |  |
| Rol Calcitonin[2] |  | K | L | Q | T | Y | P | R | T | D | V | G | A | G | T | P—NH$_2$ |
| Chicken Calcitonin[3] |  | K | L | Q | T | Y | P | R | T | D | V | G | A | G | T | P—NH$_2$ |
| UGP302[4] |  | K | L | Q | T | Y | P | R | T | D | V | G | A | N | A | P—NH$_2$ |

[1]SEQ ID NO: 1
[2]SEQ ID NO: 2
[3]SEQ ID NO: 3
[4]SEQ ID NO: 4

Peptide UGP302 of WO2013/067357 is also referred to herein under the name KBP-042.

There is a continuing need to develop calcitonin analogues having still further improved properties, or at least providing alternative artificial sequences improving on the properties of the naturally occurring calcitonins, particularly in respect of amylin and calcitonin receptor agonism, while eliminating CGRP-Receptor agonism, and thereby ensuring the optimal in vivo efficacy to safety ratio.

Peptide sequences of relevance include

TABLE 2

|  | 1 | 2 | 3 | 4 | 5 | 6 | 7 | 8 | 9 | 10 | 11 | 12 | 13 | 14 | 15 | 16 | 17 |
|---|---|---|---|---|---|---|---|---|---|---|---|---|---|---|---|---|---|
| SEQ ID NO: 53 | C | A | S | L | S | T | C | X$^a$ | L | G | X$^b$ | L | S | Q | X$^c$ | L | H |
| SEQ ID NO: 8 | C | S | N | L | S | T | C | M | L | G | R | L | S | Q | X$^c$ | L | H |

|  | 18 | 19 | 20 | 21 | 22 | 23 | 24 | 25 | 26 | 27 | 28 | 29 | 30 | 31 | 32 |
|---|---|---|---|---|---|---|---|---|---|---|---|---|---|---|---|
| SEQ ID NO: 53 | X$^d$ | L | Q | X$^e$ | X$^f$ | P | X$^g$ | T | D | V | G | A | N | A | X$^h$ |
| SEQ ID NO: 8 | R | L | Q | X$^e$ | X$^f$ | P | K | T | D | V | G | A | N | A | X$^h$ | wherein, independently, X$^a$ is V or M; X$^b$ is K or R; X$^c$ is either D or E; X$^d$ is K or R; X$^e$ is T or S; X$^f$ is F or Y; X$^g$ is K or R; and X$^h$ is P or Y, P being preferred.

Others of interest are shown in the following tables:

TABLE 2a

|  | 1 | 2 | 3 | 4 | 5 | 6 | 7 | 8 | 9 | 10 | 11 | 12 | 13 | 14 | 15 | 16 | 17 |
|---|---|---|---|---|---|---|---|---|---|---|---|---|---|---|---|---|---|
| SEQ ID NO: 5 | C | A | S | L | S | T | C | V | L | G | R | L | S | Q | X$^c$ | L | H |
| SEQ ID NO: 6 | C | A | S | L | S | T | C | M | L | G | K | L | T | Q | X$^c$ | L | H |
| SEQ ID NO: 7 (KBP-056/057) | C | A | S | L | S | T | C | V | L | G | K | L | S | Q | X$^c$ | L | H |
| SEQ ID NO: 8 (KBP-088/089) | C | S | N | L | S | T | C | M | L | G | R | L | S | Q | X$^c$ | L | H |
| SEQ ID NO: 54 | C | A | S | L | S | T | C | M | L | G | R | L | S | Q | X$^c$ | L | H |
| SEQ ID NO: 55 | C | A | S | L | S | T | C | M | L | G | K | L | T | Q | X$^c$ | L | H |
| SEQ ID NO: 56 | C | A | S | L | S | T | C | V | L | G | K | L | S | Q | X$^c$ | L | H |
| SEQ ID NO: 57 | C | S | N | L | S | T | C | V | L | C | R | L | S | Q | X$^c$ | L | H |
| SEQ ID NO: 58 (KBP-017) | C | A | S | L | S | T | C | V | L | G | K | L | S | Q | X$^c$ | L | H |
| SEQ ID NO: 59 (KBP-018) | C | A | S | L | S | T | C | V | L | G | K | L | S | Q | X$^c$ | L | H |

|  | 18 | 19 | 20 | 21 | 22 | 23 | 24 | 25 | 26 | 27 | 28 | 29 | 30 | 31 | 32 |
|---|---|---|---|---|---|---|---|---|---|---|---|---|---|---|---|
| SEQ ID NO: 5 | R | L | Q | T | X$^e$ | P | R | T | D | V | G | A | N | A | P |
| SEQ ID NO: 6 | K | L | Q | T | X$^e$ | P | R | P | D | V | G | A | N | A | P |
| SEQ ID NO: 7 (KBP-056/057) | K | L | Q | T | X$^e$ | P | K | T | D | V | G | A | N | A | P |

TABLE 2a-continued

| | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| SEQ ID NO: 8 (KBP-088/089) | R | L | Q | T | $X^e$ | P | K | T | D | V | G | A | N | A | P |
| SEQ ID NO: 54 | R | L | Q | T | $X^e$ | P | K | T | D | V | G | A | N | A | P |
| SEQ ID NO: 55 | K | L | Q | T | $X^e$ | P | K | T | D | V | G | A | N | A | P |
| SEQ ID NO: 56 | K | L | Q | T | $X^e$ | P | R | T | D | V | G | A | N | A | P |
| SEQ ID NO: 57 | R | L | Q | T | $X^e$ | P | K | T | D | V | G | A | N | A | P |
| SEQ ID NO: 58 (KBP-017) | K | L | Q | S | $X^e$ | P | K | T | D | V | G | A | N | A | P |
| SEQ ID NO: 59 (KBP-018) | K | L | Q | T | $X^e$ | P | K | T | D | V | G | A | N | A | P | wherein $X^c$ is either D or E and $X^e$ is independently either F or Y and each of which sequences may be carboxylated at its N-terminal or otherwise modified to reduce the positive charge of the first amino acid and independently of that may be animated at its C-terminal, and in each of which the 1 and 7 position cysteine residues may together be replaced by α-aminosuberic acid (Asu).

TABLE 2b

| | 1 | 2 | 3 | 4 | 5 | 6 | 7 | 8 | 9 | 10 | 11 | 12 | 13 | 14 | 15 | 16 | 17 |
|---|---|---|---|---|---|---|---|---|---|---|---|---|---|---|---|---|---|
| SEQ ID NO: 28 (KBP-011) | C | A | S | L | S | T | C | V | L | G | R | L | S | Q | E | L | H |
| SEQ ID NO: 29 | C | A | S | L | S | T | C | M | L | G | K | L | T | Q | E | L | H |
| SEQ ID NO: 30 (KBP-018) | C | A | S | L | S | T | C | V | L | G | K | L | S | Q | E | L | H |
| SEQ ID NO: 31 (KBP-088) | C | S | N | L | S | T | C | M | L | G | R | L | S | Q | E | L | H |
| SEQ ID NO: 32 | C | A | S | L | S | T | C | V | L | G | R | L | S | Q | E | L | H |
| SEQ ID NO: 33 | C | A | S | L | S | T | C | M | L | G | K | L | T | Q | E | L | H |
| SEQ ID NO: 34 | C | A | S | L | S | T | C | V | L | G | K | L | S | Q | E | L | H |
| SEQ ID NO: 35 (KBP-021) | C | S | N | L | S | T | C | M | L | G | R | L | S | Q | E | L | H |
| SEQ ID NO: 36 | C | A | S | L | S | T | C | V | L | G | R | L | S | Q | D | L | H |
| SEQ ID NO: 37 | C | A | S | L | S | T | C | M | L | G | K | L | T | Q | D | L | H |
| SEQ ID NO: 38 (KBP-056) | C | A | S | L | S | T | C | V | L | G | K | L | S | Q | D | L | H |
| SEQ ID NO: 39 | C | S | N | L | S | T | C | M | L | G | R | L | S | Q | D | L | H |
| SEQ ID NO: 40 | C | A | S | L | S | T | C | V | L | G | R | L | S | Q | D | L | H |
| SEQ ID NO: 41 | C | A | S | L | S | T | C | M | L | G | K | L | T | Q | D | L | H |
| SEQ ID NO: 42 (KBP-057) | C | A | S | L | S | T | C | V | L | G | K | L | S | Q | D | L | H |
| 089 SEQ ID NO: 43 | C | S | N | L | S | T | C | M | L | G | R | L | S | Q | D | L | H |
| SEQ ID NO: 60 | C | A | S | L | S | T | C | V | L | G | R | L | S | Q | E | L | H |
| SEQ ID NO: 61 | C | A | S | L | S | T | C | M | L | G | K | L | T | Q | E | L | H |
| SEQ ID NO: 62 | C | A | S | L | S | T | C | V | L | G | K | L | S | Q | E | L | H |
| SEQ ID NO: 63 | C | S | N | L | S | T | C | M | L | G | R | L | S | Q | E | L | H |
| SEQ ID NO: 64 | C | A | S | L | S | T | C | V | L | G | R | L | S | Q | E | L | H |
| SEQ ID NO: 65 | C | A | S | L | S | T | C | M | L | G | K | L | T | Q | E | L | H |
| SEQ ID NO: 66 | C | A | S | L | S | T | C | V | L | G | K | L | S | Q | E | L | H |
| SEQ ID NO: 67 | C | S | N | L | S | T | C | M | L | G | R | L | S | Q | E | L | H |
| SEQ ID NO: 68 | C | A | S | L | S | T | C | V | L | G | R | L | S | Q | D | L | H |
| SEQ ID NO: 69 | C | A | S | L | S | T | C | M | L | G | K | L | T | Q | D | L | H |
| SEQ ID NO: 70 | C | A | S | L | S | T | C | V | L | G | K | L | S | Q | D | L | H |
| SEQ ID NO: 71 | C | S | N | L | S | T | C | M | L | G | R | L | S | Q | D | L | H |
| SEQ ID NO: 72 | C | A | S | L | S | T | C | V | L | G | R | L | S | Q | D | L | H |
| SEQ ID NO: 73 | C | A | S | L | S | T | C | M | L | G | K | L | T | Q | D | L | H |
| SEQ ID NO: 74 (KBP-017) | C | A | S | L | S | T | C | V | L | G | K | L | S | Q | D | L | H |
| SEQ ID NO: 75 | C | S | N | L | S | T | C | M | L | G | R | L | S | Q | D | L | H |
| SEQ ID NO: 76 | C | S | N | L | S | T | C | V | L | G | K | L | S | Q | E | L | H |
| SEQ ID NO: 77 (KBP-019) | C | A | S | L | S | T | C | M | L | G | R | L | S | Q | D | L | H |

| | 18 | 19 | 20 | 21 | 22 | 23 | 24 | 25 | 26 | 27 | 28 | 29 | 30 | 31 | 32 |
|---|---|---|---|---|---|---|---|---|---|---|---|---|---|---|---|
| SEQ ID NO: 28 (KBP-011) | R | | L | Q | T | F | P | R | T | D | V | G | A | N | A | P |
| SEQ ID NO: 29 | K | | L | Q | T | F | P | R | T | D | V | G | A | N | A | P |
| SEQ ID NO: 30 (KBP-018) | K | | L | Q | T | F | P | K | T | D | V | G | A | N | A | P |
| SEQ ID NO: 31 (KBP-088) | R | | L | Q | T | F | P | K | T | D | V | G | A | N | A | P |
| SEQ ID NO: 32 | R | | L | Q | T | Y | P | R | T | D | V | G | A | N | A | P |
| SEQ ID NO: 33 | K | | L | Q | T | Y | P | R | T | D | V | G | A | N | A | P |
| SEQ ID NO: 34 | K | | L | Q | T | Y | P | K | T | D | V | G | A | N | A | P |

TABLE 2b-continued

| | | | | | | | | | | | | | |
|---|---|---|---|---|---|---|---|---|---|---|---|---|---|
| SEQ ID NO: 35 (KBP-021) | R | L | Q | T | Y | P | K | T | D | V | G | A | N | A | P |
| SEQ ID NO: 36 | R | L | Q | T | F | P | R | T | D | V | G | A | N | A | P |
| SEQ ID NO: 37 | K | L | Q | T | F | P | R | T | D | V | G | A | N | A | P |
| SEQ ID NO: 38 (KBP-056) | K | L | Q | T | F | P | K | T | D | V | G | A | N | A | P |
| SEQ ID NO: 39 | R | L | Q | T | F | P | R | T | D | V | G | A | N | A | P |
| SEQ ID NO: 40 | R | L | Q | T | Y | P | R | T | D | V | G | A | N | A | P |
| SEQ ID NO: 41 | K | L | Q | T | Y | P | R | T | D | V | G | A | N | A | P |
| SEQ ID NO: 42 (KBP-057) | K | L | Q | T | Y | P | K | T | D | V | G | A | N | A | P |
| 089 SEQ ID NO: 43 | R | L | Q | T | Y | P | K | T | D | V | G | A | N | A | P |
| SEQ ID NO: 60 | R | L | Q | S | F | P | R | T | D | V | G | A | N | A | P |
| SEQ ID NO: 61 | K | L | Q | S | F | P | R | T | D | V | G | A | N | A | P |
| SEQ ID NO: 62 | K | L | Q | S | F | P | K | T | D | V | G | A | N | A | P |
| SEQ ID NO: 63 | R | L | Q | S | F | P | K | T | D | V | G | A | N | A | P |
| SEQ ID NO: 64 | R | L | Q | S | Y | P | R | T | D | V | G | A | N | A | P |
| SEQ ID NO: 65 | K | L | Q | S | Y | P | R | T | D | V | G | A | N | A | P |
| SEQ ID NO: 66 | K | L | Q | S | Y | P | K | T | D | V | G | A | N | A | P |
| SEQ ID NO: 67 | R | L | Q | S | Y | P | K | T | D | V | G | A | N | A | P |
| SEQ ID NO: 68 | R | L | Q | S | F | P | R | T | D | V | G | A | N | A | P |
| SEQ ID NO: 69 | K | L | Q | S | F | P | R | T | D | V | G | A | N | A | P |
| SEQ ID NO: 70 | K | L | Q | S | F | P | K | T | D | V | G | A | N | A | P |
| SEQ ID NO: 71 | R | L | Q | S | F | P | K | T | D | V | G | A | N | A | P |
| SEQ ID NO: 72 | R | L | Q | S | Y | P | R | T | D | V | G | A | N | A | P |
| SEQ ID NO: 73 | K | L | Q | S | Y | P | R | T | D | V | G | A | N | A | P |
| SEQ ID NO: 74 (KBP-017) | K | L | Q | S | Y | P | K | T | D | V | G | A | N | A | P |
| SEQ ID NO: 75 | R | L | Q | S | Y | P | K | T | D | V | G | A | N | A | P |
| SEQ ID NO: 76 | K | L | Q | T | Y | P | R | T | D | V | G | A | N | A | P |
| SEQ ID NO: 77 (KBP-019) | R | L | Q | T | Y | P | K | T | D | V | G | A | N | A | P |

TABLE 3

| | 1 | 2 | 3 | 4 | 5 | 6 | 7 | 8 | 9 | 10 | 11 | 12 | 13 | 14 | 15 | 16 | 17 |
|---|---|---|---|---|---|---|---|---|---|---|---|---|---|---|---|---|---|
| SEQ ID NO: 9 (KBP-011) | AcC | A | S | L | S | T | C | V | L | G | R | L | S | Q | E | L | H |
| SEQ ID NO: 78 (KBP-017) | AcC | A | S | L | S | T | C | V | L | G | K | L | S | Q | D | L | H |
| (SEQ ID NO: 79 (KBP-018) | AcC | A | S | L | S | T | C | V | L | G | K | L | S | Q | E | L | H |
| SEQ ID NO :10 (KBP-023) | AcC | A | S | L | S | T | C | M | L | G | K | L | T | Q | E | L | H |
| SEQ ID NO: 11 (KBP-056) | AcC | A | S | L | S | T | C | V | L | G | K | L | S | Q | D | L | H |
| SEQ ID NO: 80 (KBP-057) | AcC | A | S | L | S | T | C | V | L | G | K | L | S | Q | D | L | H |
| SEQ ID NO: 12 (KBP-088) | AcC | S | N | L | S | T | C | M | L | G | R | L | S | Q | E | L | H |
| SEQ ID NO: 44 (KBP-089) | AcC | S | N | L | S | T | C | M | L | G | R | L | S | Q | D | L | H |

| | 18 | 19 | 20 | 21 | 22 | 23 | 24 | 25 | 26 | 27 | 28 | 29 | 30 | 31 | 32 |
|---|---|---|---|---|---|---|---|---|---|---|---|---|---|---|---|
| SEQ ID NO: 9 (KBP-011) | R | L | Q | T | F | P | R | T | D | V | G | A | N | A | P—NH$_2$ |
| SEQ ID NO: 78 (KBP-017) | K | L | Q | S | Y | P | K | T | D | V | G | A | N | A | P—NH$_2$ |
| (SEQ ID NO: 79 (KBP-018) | K | L | Q | T | F | P | K | T | D | V | G | A | N | A | P—NH$_2$ |
| SEQ ID NO :10 | K | L | Q | T | F | P | R | T | D | V | G | A | N | A | P—NH$_2$ |
| SEQ ID NO: 11 (KBP-056) | K | L | Q | T | F | P | R | T | D | V | G | A | N | A | P—NH$_2$ |
| SEQ ID NO: 80 (KBP-057) | K | L | Q | T | Y | P | K | T | D | V | G | A | N | A | P—NH$_2$ |
| SEQ ID NO: 12 (KBP-088) | R | L | Q | T | F | P | K | T | D | V | G | A | N | A | P—NH$_2$ |
| SEQ ID NO: 44 (KBP-089) | R | L | Q | T | Y | P | K | T | D | V | G | A | N | A | P—NH$_2$ |

TABLE 4a

| | 1 | 2 | 3 | 4 | 5 | 6 | 7 | 8 | 9 | 10 | 11 | 12 | 13 | 14 | 15 | 16 | 17 |
|---|---|---|---|---|---|---|---|---|---|---|---|---|---|---|---|---|---|
| SEQ ID NO: 45 | C | A | S | L | S | T | C | V | L | G | R | L | S | Q | $X^e$ | L | H |
| SEQ ID NO: 46 | C | A | S | L | S | T | C | M | L | G | K | L | T | Q | $X^e$ | L | H |
| SEQ ID NO: 47 | C | A | S | L | S | T | C | V | L | G | K | L | S | Q | $X^e$ | L | H |
| SEQ ID NO: 48 | C | S | N | L | S | T | C | M | L | G | R | L | S | Q | $X^e$ | L | H |
| SEQ ID NO: 49 | C | A | S | L | S | T | C | V | L | G | R | L | S | Q | $X^e$ | L | H |
| SEQ ID NO: 50 | C | A | S | L | S | T | C | M | L | G | K | L | T | Q | $X^e$ | L | H |
| SEQ ID NO: 51 | C | A | S | L | S | T | C | V | L | G | R | L | S | Q | $X^e$ | L | H |
| SEQ ID NO: 52 | C | A | S | L | S | T | C | M | L | G | K | L | T | Q | $X^e$ | L | H |

| | 18 | 19 | 20 | 21 | 22 | 23 | 24 | 25 | 26 | 27 | 28 | 29 | 30 | 31 | 32 |
|---|---|---|---|---|---|---|---|---|---|---|---|---|---|---|---|
| SEQ ID NO: 45 | R | L | Q | T | $X^e$ | P | K | T | D | V | G | A | N | A | Y |
| SEQ ID NO: 46 | K | L | Q | T | $X^e$ | P | K | T | D | V | G | A | N | A | Y |
| SEQ ID NO: 47 | K | L | Q | T | $X^e$ | P | K | T | D | V | G | A | N | A | Y |
| SEQ ID NO: 48 | R | L | Q | T | $X^e$ | P | K | T | D | V | G | A | N | A | Y |
| SEQ ID NO: 49 | R | L | Q | T | $X^e$ | P | R | T | D | V | G | A | N | A | Y |
| SEQ ID NO: 50 | K | L | Q | T | $X^e$ | P | R | T | D | V | G | A | N | A | Y |
| SEQ ID NO: 51 | R | L | Q | T | $X^e$ | P | K | T | D | V | G | A | N | A | P |
| SEQ ID NO: 52 | K | L | Q | T | $X^e$ | P | K | T | D | V | G | A | N | A | P | wherein $X^c$ is either D or E and $X^e$ is independently either F or Y.

TABLE 4b

| | 1 | 2 | 3 | 4 | 5 | 6 | 7 | 8 | 9 | 10 | 11 | 12 | 13 | 14 | 15 | 16 | 17 |
|---|---|---|---|---|---|---|---|---|---|---|---|---|---|---|---|---|---|
| SEQ ID NO: 20 | C | A | S | L | S | T | C | V | L | G | R | L | S | Q | E | L | H |
| SEQ ID NO: 21 | C | A | S | L | S | T | C | M | L | G | K | L | T | Q | E | L | H |
| SEQ ID NO: 22 | C | A | S | L | S | T | C | V | L | G | K | L | S | Q | D | L | H |
| SEQ ID NO: 23 | C | A | S | L | S | T | C | M | L | G | R | L | S | Q | E | L | H |
| SEQ ID NO: 24 | C | A | S | L | S | T | C | V | L | G | R | L | S | Q | E | L | H |
| SEQ ID NO: 25 | C | A | S | L | S | T | C | M | L | G | K | L | T | Q | E | L | H |
| SEQ ID NO: 26 | C | A | S | L | S | T | C | V | L | G | R | L | S | Q | E | L | H |
| SEQ ID NO: 27 | C | A | S | L | S | T | C | M | L | G | K | L | T | Q | E | L | H |

| | 18 | 19 | 20 | 21 | 22 | 23 | 24 | 25 | 26 | 27 | 28 | 29 | 30 | 31 | 32 |
|---|---|---|---|---|---|---|---|---|---|---|---|---|---|---|---|
| SEQ ID NO: 20 | R | L | Q | T | F | P | K | T | D | V | G | A | N | A | Y |
| SEQ ID NO: 21 | K | L | Q | T | F | P | K | T | D | V | G | A | N | A | Y |
| SEQ ID NO: 22 | K | L | Q | T | F | P | K | T | D | V | G | A | N | A | Y |
| SEQ ID NO: 23 | R | L | Q | T | F | P | K | T | D | V | G | A | N | A | Y |
| SEQ ID NO: 24 | R | L | Q | T | F | P | R | T | D | V | G | A | N | A | Y |
| SEQ ID NO: 25 | K | L | Q | T | F | P | R | T | D | V | G | A | N | A | Y |
| SEQ ID NO: 26 | K | L | Q | T | F | P | K | T | D | V | G | A | N | A | P |
| SEQ ID NO: 27 | R | L | Q | T | F | P | K | T | D | V | G | A | N | A | P |

Accordingly the present invention now provides a peptide having any one of the amino acid sequences of Table 2a or Table 4a each of which may be carboxylated at its N-terminal or otherwise modified to reduce the positive charge of the first amino acid and independently of that may be amidated at its C-terminal, and in each of which the 1 and 7 position cysteine residues may together be replaced by α-aminosuberic acid (Asu).

The invention includes a peptide having any one of the amino acid sequences of Table 3.

The invention also includes a peptide having any one of the amino acid sequences of Table 2b or Table 4b each of which may be carboxylated at its N-terminal or otherwise modified to reduce the positive charge of the first amino acid and independently of that may be amidated at its C-terminal, and in each of which the 1 and 7 position cysteine residues may together be replaced by α-aminosuberic acid (Asu).

Having investigated the activity of numerous 32 amino acid analogs of natural calcitonins particularly looking into which amino acids are needed for the potent activation of the receptor-mediated responses, we have found that the amino acids numbered: 11, 15, 18, 22, 24, 30 and 31 are more stringent in terms of amino acid type, with preferred values for 11 being a K or an R, 15 a D or an E, 18 a K or an R, 22 a Y or an F, 24 preferably a K although an R works, 30 an N and 31 an A.

The peptide may be formulated for administration as a pharmaceutical and may be formulated for enteral or parenteral administration. Preferred formulations are injectable, preferably for subcutaneous injection, however the peptide may be formulated with a carrier for oral administration, and optionally wherein the carrier increases the oral bioavailability of the peptide. Suitable carriers include ones that comprise 5-CNAC, SNAD, or SNAC.

Optionally, the peptide is formulated in a pharmaceutical composition for oral administration comprising coated citric acid particles, and wherein the coated citric acid particles increases the oral bioavailability of the peptide.

The invention includes a peptide of the invention for use as a medicament. The peptide may be for use in treating diabetes (Type I and/or Type II), excess bodyweight, excessive food consumption, metabolic syndrome, rheumatoid arthritis, non-alcoholic fatty liver disease, osteoporosis, or osteoarthritis, poorly regulated blood glucose levels, poorly regulated response to glucose tolerance tests, or poorly regulated of food intake. In particular, the peptides may be used to lower an undesirably high fasting blood glucose level or to lower an undesirably high HbA1c or to reduce an undesirably high response to a glucose tolerance test.

In some embodiments, the N-terminal side of the calcitonin mimetics discussed supra is modified to reduce the positive charge of the first amino acid. For example, an acetyl, propionyl, or succinyl group may be substituted on cysteine-1. In Table 3, "Ac" refers to an acetyl group modification. Each 'Ac' in Table 3 may be replaced by "Pr" referring to a propionyl group modification, or by "Succ" referring to a succinyl group modification. "$NH_2$" refers to an amidated C-terminal carboxylic acid group. Alternative ways of reducing positive charge include, but are not limited to, polyethylene glycol-based PEGylation, or the addition of another amino acid such as glutamic acid or aspartic acid at the N-terminus. Alternatively, other amino acids may be added to the N-terminus of peptides discussed supra including, but not limited to, lysine, glycine, formylglycine, leucine, alanine, acetyl alanine, and dialanyl. As those of skill in the art will appreciate, peptides having a plurality of cysteine residues frequently form a disulfide bridge between two such cysteine residues. All such peptides set forth herein are defined as optionally including one or more such disulphide bridges, particularly at the Cys1-Cys7 locations. Mimicking this, the cysteines at positions 1 and 7 may jointly be replaced by an α-aminosuberic acid linkage. All peptides disclosed herein that have KBP-0## numbers have such a disulphide bridge.

While calcitonin mimetics of the present disclosure may exist in free acid form, it is preferred that the C-terminal amino acid be amidated. Applicants expect that such amidation may contribute to the effectiveness and/or bioavailability of the peptide. A preferred technique for manufacturing amidated versions of the calcitonin mimetics of the present disclosure is to react precursors (having glycine in place of the C-terminal amino group of the desired amidated product) in the presence of peptidylglycine alpha-amidating monooxygenase in accordance with known techniques wherein the precursors are converted to amidated products in reactions described, for example, in U.S. Pat. No. 4,708,934 and EP0308067 and EP0382403.

Recombinant production is preferred for both the precursor and the enzyme that catalyzes the conversion of the precursor to salmon calcitonin. Such recombinant production is discussed in Biotechnology, Vol. 11 (1993) pp. 64-70, by Ray M V, Van Duyne P, Bertelsen A H, Jackson-Matthews D E, Sturmer A M, Merkler D J, Consalvo A P, Young S D, Gilligan J P, Shields P P. which further describes a conversion of a precursor to an amidated product. The recombinant product reported there is identical to natural salmon calcitonin, and to salmon calcitonin produced using solution and solid phase chemical peptide synthesis.

Production of amidated products may also be accomplished using the process and amidating enzyme set forth by Consalvo, et al in U.S. Pat. No. 7,445,911; Miller et al, US2006/0292672; Ray et al, 2002, Protein Expression and Purification, 26:249-259; and Mehta, 2004, Biopharm. International, July, pp. 44-46.

The production of the preferred amidated peptides may proceed, for example, by producing glycine-extended precursor in E. coli as a soluble fusion protein with glutathione-S-transferase, or by direct expression of the precursor in accordance with the technique described in U.S. Pat. No. 6,103,495. Such a glycine extended precursor has a molecular structure that is identical to the desired amidated product except at the C-terminus (where the product terminates —X—$NH_2$, while the precursor terminates —X-gly, X being the C-terminal amino acid residue of the product). An alpha-amidating enzyme described in the publications above catalyzes conversion of precursors to product. That enzyme is preferably recombinantly produced, for example, in Chinese Hamster Ovary (CHO) cells), as described in the Biotechnology and Biopharm. articles cited above.

Free acid forms of peptide active agents of the present disclosure may be produced in like manner, except without including a C-terminal glycine on the "precursor", which precursor is instead the final peptide product and does not require the amidation step.

Except where otherwise stated, the preferred dosage of the calcitonin mimetics of the present disclosure is identical for both therapeutic and prophylactic purposes.

Desired dosages are discussed in more detail, infra, and differ depending on mode of administration.

Except where otherwise noted or where apparent from context, dosages herein refer to weight of active compounds unaffected by or discounting pharmaceutical excipients, diluents, carriers or other ingredients, although such additional ingredients are desirably included. Any dosage form (capsule, tablet, injection or the like) commonly used in the pharmaceutical industry for delivery of peptide active agents is appropriate for use herein, and the terms "excipient", "diluent", or "carrier" includes such non-active ingredients as are typically included, together with active ingredients in such dosage form in the industry. A preferred oral dosage form is discussed in more detail, infra, but is not to be considered the exclusive mode of administering the active agents of the present disclosure.

The calcitonin mimetics of the present disclosure can be administered to a patient to treat a number of diseases or disorders. As used herein, the term "patient" means any organism belonging to the kingdom Animalia. In an embodiment, the term "patient" refers to vertebrates, more preferably, mammals including humans.

Accordingly, the present disclosure includes the use of the peptides in a method of treatment of type I diabetes, Type II diabetes or metabolic syndrome, obesity, or of appetite suppression, or for mitigating insulin resistance, or for reducing an undesirably high fasting serum glucose level, or for reducing an undesirably high peak serum glucose level, or for reducing an undesirably high peak serum insulin level, or for reducing an undesirably large response to a glucose tolerance test, or for treating osteoporosis, or for treating osteoarthritis.

There are a number of art-recognized measures of normal range for body weight in view of a number of factors such as gender, age and height. A patient in need of treatment or prevention regimens set forth herein include patients whose body weight exceeds recognized norms or who, due to heredity, environmental factors or other recognized risk factor, are at higher risk than the general population of becoming overweight or obese. In accordance with the present disclosure, it is contemplated that the calcitonin mimetics may be used to treat diabetes where weight control is an aspect of the treatment.

In an embodiment, the method includes enteral administration to a patient in need thereof for treatment of a said condition of a pharmaceutically effective amount of any one of the peptides described herein.

In an embodiment, the method includes parenteral administration to a patient in need thereof for treatment of a said condition of a pharmaceutically effective amount of any one of the peptides described herein. For parenteral administration (including intraperitoneal, subcutaneous, intravenous, intradermal or intramuscular injection), solutions of a peptide of the present disclosure in either sesame or peanut oil or in aqueous propylene glycol may be employed, for example. The aqueous solutions should be suitably buffered (preferably pH greater than 8) if necessary and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art. For parenteral application, examples of suitable preparations include solutions, preferably oily or aqueous solutions as well as suspensions, emulsions, or implants, including suppositories. Peptides may be formulated in sterile form in multiple or single dose formats such as being dispersed in a fluid carrier such as sterile physiological saline or 5% saline dextrose solutions commonly used with injectables.

Said method may include a preliminary step of determining whether the patient suffers from a said condition, and/or a subsequent step of determining to what extent said treatment is effective in mitigating the condition in said patient, e.g. in each case, carrying out an oral glucose tolerance test or a resting blood sugar level.

For improved control over the weight of the patient, to produce a loss of weight or an avoidance of weight gain, the active compound is preferably administered once daily or more such as at least twice per day, e.g. from 2-4 times per day. Formulations of the active compound may contain a unit dosage appropriate for such an administration schedule. The active compounds may be administered with a view to controlling the weight of a patient undergoing treatment for diabetes or metabolic syndrome.

Oral enteral formulations are for ingestion by swallowing for subsequent release in the intestine below the stomach, and hence delivery via the portal vein to the liver, as opposed to formulations to be held in the mouth to allow transfer to the bloodstream via the sublingual or buccal routes.

Suitable dosage forms for use in the present disclosure include tablets, mini-tablets, capsules, granules, pellets, powders, effervescent solids and chewable solid formulations. Such formulations may include gelatin which is preferably hydrolysed gelatin or low molecular weight gelatin. Such formulations may be obtainable by freeze drying a homogeneous aqueous solution comprising calcitonin or a fragment or conjugate thereof and hydrolysed gelatin or low molecular weight gelatin and further processing the resulting solid material into said oral pharmaceutical formulation, and wherein the gelatin may have a mean molecular weight from 1000 to 15000 Daltons. Such formulations may include a protective carrier compound such as 5-CNAC or others as disclosed herein.

Whilst oral formulations such as tablets and capsules are preferred, compositions for use in the present disclosure may take the form of syrups, elixirs or the like and suppositories or the like. Oral delivery is generally the delivery route of choice since it is convenient, relatively easy and generally painless, resulting in greater patient compliance relative to other modes of delivery. However, biological, chemical and physical barriers such as varying pH in the gastrointestinal tract, powerful digestive enzymes, and active agent impermeable gastrointestinal membranes, makes oral delivery of calcitonin like peptides to mammals problematic, e.g. the oral delivery of calcitonins, which are long-chain polypeptide hormones secreted by the parafollicular cells of the thyroid gland in mammals and by the ultimobranchial gland of birds and fish, originally proved difficult due, at least in part, to the insufficient stability of calcitonin in the gastrointestinal tract as well as the inability of calcitonin to be readily transported through the intestinal walls into the blood stream.

Suitable oral formulations are however described below.
Treatment of Patients

In an embodiment, a calcitonin mimetic of the present disclosure is administered at adequate dosage to maintain serum levels of the mimetic in patients between 5 picograms and 500 nanograms per milliliter, preferably between 50 picograms and 250 nanograms, e.g. between 1 and 100 nanograms per milliliter. The serum levels may be measured by radioimmunoassay techniques known in the art. The attending physician may monitor patient response, and may then alter the dosage somewhat to account for individual patient metabolism and response. Near simultaneous release is best achieved by administering all components of the present disclosure as a single pill or capsule. However, the disclosure also includes, for example, dividing the required amount of the calcitonin mimetic among two or more tablets or capsules which may be administered together such that they together provide the necessary amount of all ingredients. "Pharmaceutical composition," as used herein includes but is not limited to a complete dosage appropriate to a particular administration to a patient regardless of whether one or more tablets or capsules (or other dosage forms) are recommended at a given administration.

A calcitonin mimetic of the present disclosure may be formulated for oral administration using the methods employed in the Unigene Enteripep® products. These may include the methods as described in U.S. Pat. No. 5,912,014, U.S. Pat. No. 6,086,918, U.S. Pat. No. 6,673,574, U.S. Pat. No. 7,316,819, U.S. Pat. No. 8,093,207, and US Publication No. 2009/0317462. In particular, it may include the use of conjugation of the compound to a membrane translocator such as the protein transduction domain of the HIV TAT protein, co-formulation with one or more protease inhibitors, and/or a pH lowering agent which may be coated and/or an acid resistant protective vehicle and/or an absorption enhancer which may be a surfactant.

In an embodiment, a calcitonin mimetic of the present disclosure is preferably formulated for oral delivery in a manner known in U.S. Patent Publication No. 2009/0317462. One preferred oral dosage form in accordance with the present disclosure is set forth in Table 5 below:

TABLE 5

| COMPONENTS OF A SOLID DOSAGE FORMULATION | |
|---|---|
| ACTIVE AGENT OR EXCIPIENT | FUNCTION |
| A Calcitonin Mimetic selected from one of SEQ ID NO: 1-8 | Active agent |
| Coated Citric Acid Particles | Protease Inhibitor |
| Lauroylcarnitine | Absorption Enhancer |
| Nonionic Polymer | Subcoat |
| Eudragit L30D-55 | Enteric Coat |

In an embodiment, a calcitonin mimetic of the present disclosure may be formulated for enteral, especially oral, administration by admixture with a suitable carrier compound. Suitable carrier compounds include those described in U.S. Pat. No. 5,773,647 and U.S. Pat. No. 5,866,536 and amongst these, 5-CNAC (N-(5-chlorosalicyloyl)-8-aminocaprylic acid, commonly as its disodium salt) is particularly effective. Other preferred carriers or delivery agents are SNAD (sodium salt of 10-(2-Hydroxybenzamido)decanoic acid) and SNAC (sodium salt of N-(8-[2-hydroxybenzoyl]amino)caprylic acid). In an embodiment, a pharmaceutical composition of the present disclosure comprises a delivery effective amount of carrier such as 5-CNAC, i.e. an amount sufficient to deliver the compound for the desired effect. Generally, the carrier such as 5-CNAC is present in an amount of 2.5% to 99.4% by weight, more preferably 25% to 50% by weight of the total composition.

In addition, WO 00/059863 discloses the disodium salts of formula I

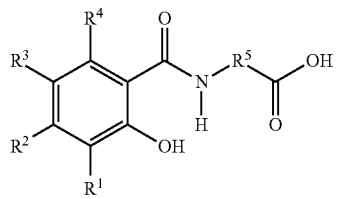

wherein
$R^1$, $R^2$, $R^3$, and $R^4$ are independently hydrogen, —OH, —$NR^6R^7$, halogen, $C_1$-$C_4$ alkyl, or $C_1$-$C_4$ alkoxy;
$R^5$ is a substituted or unsubstituted $C_2$-$C_{16}$ alkylene, substituted or unsubstituted $C_2$-$C_{16}$ alkenylene, substituted or unsubstituted $C_1$-$C_{12}$ alkyl(arylene), or substituted or unsubstituted aryl ($C_1$-$C_{12}$ alkylene); and $R^6$ and $R^7$ are independently hydrogen, oxygen, or $C_1$-$C_4$ alkyl; and hydrates and solvates thereof as particularly efficacious for the oral delivery of active agents, such as calcitonins, e.g. salmon calcitonin, and these may be used in the present disclosure.

Preferred enteric formulations using optionally micronised 5-CNAC may be generally as described in WO2005/014031.

The compound may be formulated for oral administration using the methods employed in the Capsitonin product of Bone Medical Limited. These may include the methods incorporated in Axcess formulations. More particularly, the active ingredient may be encapsulated in an enteric capsule capable of withstanding transit through the stomach. This may contain the active compound together with a hydrophilic aromatic alcohol absorption enhancer, for instance as described in WO02/028436. In a known manner the enteric coating may become permeable in a pH sensitive manner, e.g. at a pH of from 3 to 7. WO2004/091584 also describes suitable formulation methods using aromatic alcohol absorption enhancers.

The compound may be formulated using the methods seen in the Oramed products, which may include formulation with omega-3 fatty acid as seen in WO2007/029238 or as described in U.S. Pat. No. 5,102,666.

Generally, the pharmaceutically acceptable salts (especially mono or di sodium salts), solvates (e.g. alcohol solvates) and hydrates of these carriers or delivery agents may be used.

Oral administration of the pharmaceutical compositions according to the disclosure can be accomplished regularly, e.g. once or more on a daily or weekly basis; intermittently, e.g. irregularly during a day or week; or cyclically, e.g. regularly for a period of days or weeks followed by a period without administration. The dosage form of the pharmaceutical compositions of the presently disclosed embodiments can be any known form, e.g. liquid or solid dosage forms. The liquid dosage forms include solution emulsions, suspensions, syrups and elixirs. In addition to the active compound and carrier such as 5-CNAC, the liquid formulations may also include inert excipients commonly used in the art such as, solubilizing agents e.g. ethanol; oils such as cottonseed, castor and sesame oils; wetting agents; emulsifying agents; suspending agents; sweeteners; flavourings; and solvents such as water. The solid dosage forms include capsules, soft-gel capsules, tablets, caplets, powders, granules or other solid oral dosage forms, all of which can be prepared by methods well known in the art. The pharmaceutical compositions may additionally comprise additives in amounts customarily employed including, but not limited to, a pH adjuster, a preservative, a flavorant, a taste-masking agent, a fragrance, a humectant, a tonicifier, a colorant, a surfactant, a plasticizer, a lubricant such as magnesium stearate, a flow aid, a compression aid, a solubilizer, an excipient, a diluent such as microcrystalline cellulose, e.g. Avicel PH 102 supplied by FMC corporation, or any combination thereof. Other additives may include phosphate buffer salts, citric acid, glycols, and other dispersing agents. The composition may also include one or more enzyme inhibitors, such as actinonin or epiactinonin and derivatives thereof; aprotinin, Trasylol and Bowman-Birk inhibitor. Further, a transport inhibitor, i.e. a [rho]-glycoprotein such as Ketoprofin, may be present in the compositions of the present disclosure. The solid pharmaceutical compositions of the instant disclosure can be prepared by conventional methods e.g. by blending a mixture of the active compound, the carrier such as 5-CNAC, and any other ingredients, kneading, and filling into capsules or, instead of filling into capsules, molding followed by further tableting or compression-molding to give tablets. In addition, a solid dispersion may be formed by known methods followed by further processing to form a tablet or capsule. Preferably, the ingredients in the pharmaceutical compositions of the instant disclosure are homogeneously or uniformly mixed throughout the solid dosage form.

Alternatively, the active compound may be formulated as a conjugate with said carrier, which may be an oligomer as described in US2003/0069170, e.g.

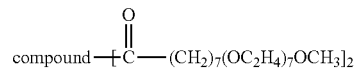

Such conjugates may be administered in combination with a fatty acid and a bile salt as described there.

Conujugates with polyethylene glycol (PEG) may be used, as described for instance in Mansoor et al.

Alternatively, active compounds may be admixed with nitroso-N-acetyl-D,L-penicillamine (SNAP) and Carbopol solution or with taurocholate and Carbapol solution to form a mucoadhesive emulsion.

The active compound may be formulated by loading into chitosan nanocapsules as disclosed in Prego et al (optionally PEG modified as in Prego Prego C, Torres D, Fernandez-Megia E, Novoa-Carballal R, Quiñoá E, Alonso M J.) or chitosan or PEG coated lipid nanoparticles as disclosed in Garcia-Fuentes et al. Chitosan nanoparticles for this purpose may be iminothiolane modified as described in Guggi et al. They may be formulated in water/oil/water emulsions as described in Dogru et al. The bioavailability of active compounds may be increased by the use of taurodeoxycholate or lauroyl carnitine as described in Sinko et al or in Song et al. Generally, suitable nanoparticles as carriers are discussed in de la Fuente et al and may be used in the present disclosure.

Other suitable strategies for oral formulation include the use of a transient permeability enhancer (TPE) system as described in WO2005/094785 of Chiasma Ltd. TPE makes use of an oily suspension of solid hydrophilic particles in a hydrophobic medium to protect the drug molecule from inactivation by the hostile gastrointestinal (GI) environment and at the same time acts on the GI wall to induce permeation of its cargo drug molecules.

Further included is the use of glutathione or compounds containing numerous thiol groups as described in US2008/0200563 to inhibit the action of efflux pumps on the mucous membrane. Practical examples of such techniques are described also in Caliceti, P. Salmaso, S., Walker, G. and Bernkop-Schnürch, A. (2004) 'Development and in vivo evaluation of an oral insulin-PEG delivery system.' Eur. J. Pharm. Sci., 22, 315-323, in Guggi, D., Krauland, A. H., and Bernkop-Schnürch, A. (2003) 'Systemic peptide delivery via the stomach: in vivo evaluation of an oral dosage form for salmon calcitonin'. J. Control. Rel. 92, 125-135, and in Bernkop-Schnürch, A., Pinter, Y., Guggi, D., Kahlbacher, H., Schöffmann, G., Schuh, M., Schmerold, I., Del Curto, M. D., D'Antonio, M., Esposito, P. and Huck, Ch. (2005) 'The use of thiolated polymers as carrier matrix in oral peptide delivery'—Proof of concept. J. Control. Release, 106, 26-33.

The active compound may be formulated in seamless micro-spheres as described in WO2004/084870 where the active pharmaceutical ingredient is solubilised as an emulsion, microemulsion or suspension formulated into minispheres; and variably coated either by conventional or novel coating technologies. The result is an encapsulated drug in "pre-solubilised" form which when administered orally provides for predetermined instant or sustained release of the active drug to specific locations and at specific rates along the gastrointestinal tract. In essence, pre-solubilization of the drug enhances the predictability of its kinetic profile while simultaneously enhancing permeability and drug stability.

One may employ chitosan coated nanocapsules as described in US2009/0074824. The active molecule administered with this technology is protected inside the nanocapsules since they are stable against the action of the gastric fluid. In addition, the mucoadhesive properties of the system enhances the time of adhesion to the intestine walls (it has been verified that there is a delay in the gastrointestinal transit of these systems) facilitating a more effective absorption of the active molecule.

Methods developed by TSR1 Inc. may be used. These include Hydrophilic Solubilization Technology (HST) in which gelatin, a naturally derived collagen extract carrying both positive and negative charges, coats the particles of the active ingredient contained in lecithin micelles and prevents their aggregation or clumping. This results in an improved wettability of hydrophobic drug particles through polar interactions. In addition, the amphiphilic lecithin reduces surface tension between the dissolution fluid and the particle surface.

The active ingredient may be formulated with cucurbiturils as excipients.

Alternatively, one may employ the GIPET technology of Merrion Pharmaceuticals to produce enteric coated tablets containing the active ingredient with an absorption enhancer which may be a medium chain fatty acid or a medium chain fatty acid derivative as described in US2007/0238707 or a membrane translocating peptide as described in U.S. Pat. No. 7,268,214.

One may employ GIRES™ technology which consists of a controlled-release dosage form inside an inflatable pouch, which is placed in a drug capsule for oral administration. Upon dissolution of the capsule, a gas-generating system inflates the pouch in the stomach. In clinical trials the pouch has been shown to be retained in the stomach for 16-24 hours.

Alternatively, the active may be conjugated to a protective modifier that allows it to withstand enzymatic degradation in the stomach and facilitate its absorption. The active may be conjugated covalently with a monodisperse, short-chain methoxy polyethylene glycol glycolipids derivative that is crystallized and lyophilized into the dry active pharmaceutical ingredient after purification. Such methods are described in U.S. Pat. No. 5,438,040 and at biocon.com.

One may also employ a hepatic-directed vesicle (HDV) for active delivery. An HDV may consist of liposomes (150 nm diameter) encapsulating the active, which also contain a hepatocyte-targeting molecule in their lipid bilayer. The targeting molecule directs the delivery of the encapsulated active to the liver cells and therefore relatively minute amounts of active are required for effect. Such technology is described in US2009/0087479 and further at diasome.com.

The active may be incorporated into a composition containing additionally a substantially non-aqueous hydrophilic medium comprising an alcohol and a cosolvent, in association with a medium chain partial glyceride, optionally in admixture with a long-chain PEG species as described in US2002/0115592 in relation to insulin.

Alternatively, use may be made of intestinal patches as described in Shen Z, Mitragotri S, Pharm Res. 2002 April; 19(4):391-5 'Intestinal patches for oral drug delivery'.

The active may be incorporated into an erodible matrix formed from a hydrogel blended with a hydrophobic polymer as described in U.S. Pat. No. 7,189,414.

Suitable oral dosage levels for adult humans to be treated may be in the range of 0.05 to 5 mg, preferably about 0.1 to 2.5 mg.

The frequency of dosage treatment of patients may be from 1 to six times daily, for instance from two to four times daily. Treatment will desirably be maintained over a prolonged period of at least 6 weeks, preferably at least 6 months, preferably at least a year, and optionally for life.

Combination treatments for relevant conditions may be carried out using a composition according to the present disclosure and separate administration of one or more other therapeutics. Alternatively, the composition according to the present disclosure may incorporate one or more other therapeutics for combined administration.

Combination therapies according to the present disclosure include combinations of an active compound as described with insulin, GLP-2, GLP-1, GIP, or amylin, or generally with other anti-diabetics. Thus combination therapies including co-formulations may be made with insulin sensitizers including biguanides such as Metformin, Buformin and Phenformin, TZD's (PPAR) such as Balaglitazone, Pioglitazone, Rivoglitazone, Rosiglitazone and Troglitazone, dual PPAR agonists such as Aleglitazar, Muraglitazar and Tesaglitazar, or secretagogues including sulphonylureas such as Carbutamide, Chlorpropamide, Gliclazide, Tolbutamide, Tolazamide, Glipizide, Glibenclamide, Glyburide, Gliquidone, Glyclopyramide and Glimepriride, Meglitinides/glinides (K+) such as Nateglinide, Repaglinide and Mitiglinide, GLP-1 analogs such as Exenatide, Liraglutide and Albiglutide, DPP-4 inhibitors such as Alogliptin, Linagliptin, Saxagliptin, Sitagliptin and Vildagliptin, insulin analogs or special formulations such as (fast acting) Insulin lispro, Insulin aspart, Insulin glulisine, (long acting) Insulin glargine, Insulin detemir), inhalable insulin—Exubra and NPH insulin, and others including alpha-glucosidase inhibitors such as Acarbose, Miglitol and Voglibose, amylin analogues such as Pramlintide, SGLT2 inhibitors such as Dapagliflozin, Remogliflozin and Sergliflozin as well as miscellaneous ones including Benfluorex and Tolrestat.

Further combinations include co-administration or co-formulation with leptins. Leptin resistance is a well-established component of type 2 diabetes; however, injections of leptin have so far failed to improve upon this condition. In contrast, there is evidence supporting that amylin, and thereby molecules with amylin-like abilities, as the salmon calcitonin mimetics, are able to improve leptin sensitivity. Amylin/leptin combination has shown a synergistic effect on body weight and food intake, and also insulin resistance [Kusakabe T et al].

The presently disclosed embodiments is described in the following Examples, which are set forth to aid in the understanding of the disclosure, and should not be construed to limit in any way the scope of the disclosure as defined in the claims which follow thereafter. The following examples are put forth so as to provide those of ordinary skill in the art with a complete disclosure and description of how to make and use the described embodiments, and are not intended to limit the scope of the present disclosure nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Results are shown in the accompanying drawings, as follows:

FIGS. 1A-1E: Raw data showing the activity of KBPs of Table 3 on the CTR head to head with sCT and UGP302/KBP-042 at different timepoints, 4 h (FIG. 1A), 8 h (FIG. 1A), 24 h (FIG. 1A), 48 h (FIG. 1A), 72 h (FIG. 1A).

Figure 2A:
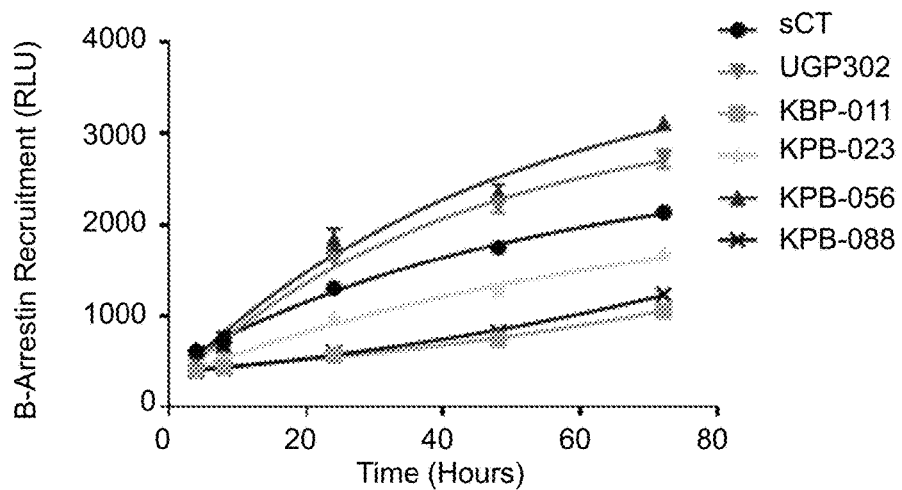
Figure 2B:
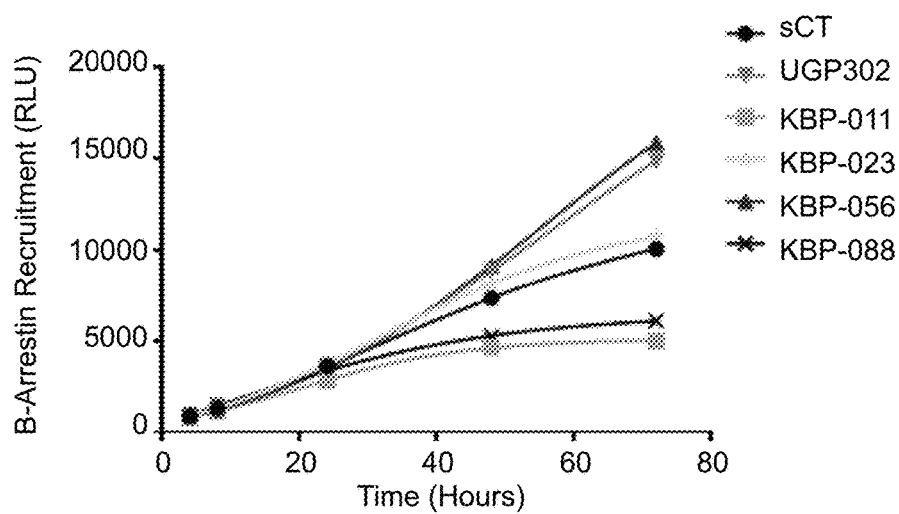
Figure 2C:
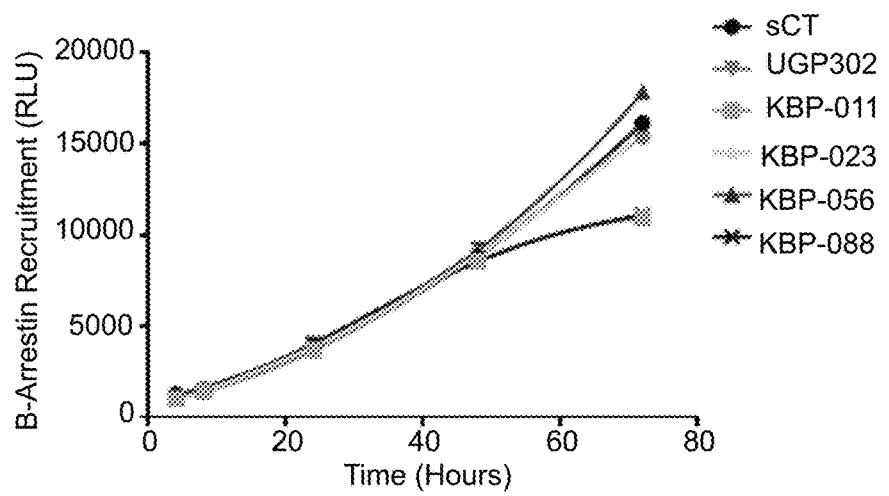

FIGS. 2A-2C: Activation of the CTR as a function of time, by fixed concentrations of the different ligands at 1 nM (FIG. 2A), 10 nM (FIG. 2B) and 100 nM (FIG. 2C) by a prolonged beta-arrestin assay.

Figure 3:
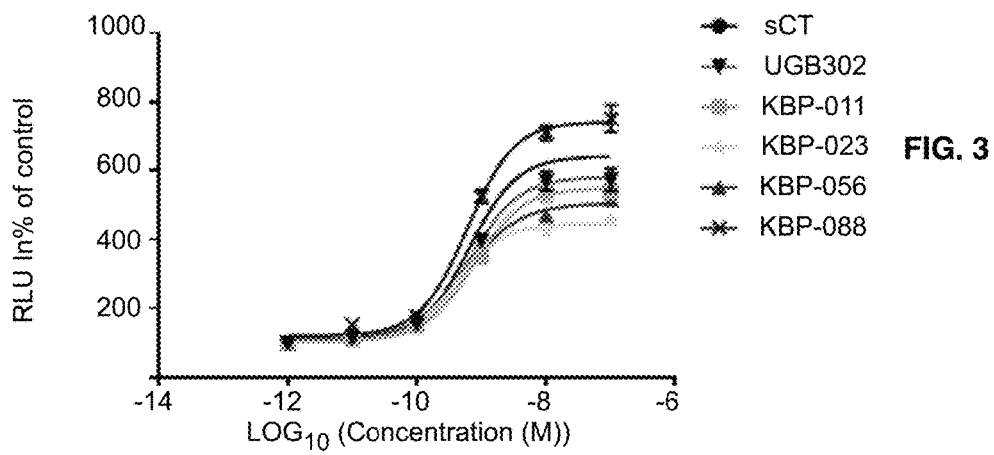

FIG. 3: Dose-response activation of the AMY-R for the different ligands when added to a cell-line expressing the AMY-R.

Figure 4A:
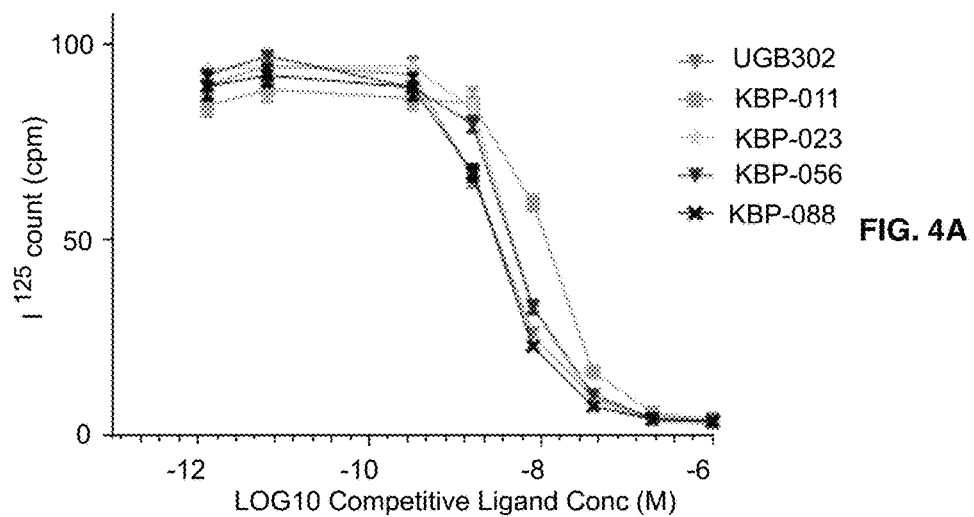
Figure 4B:
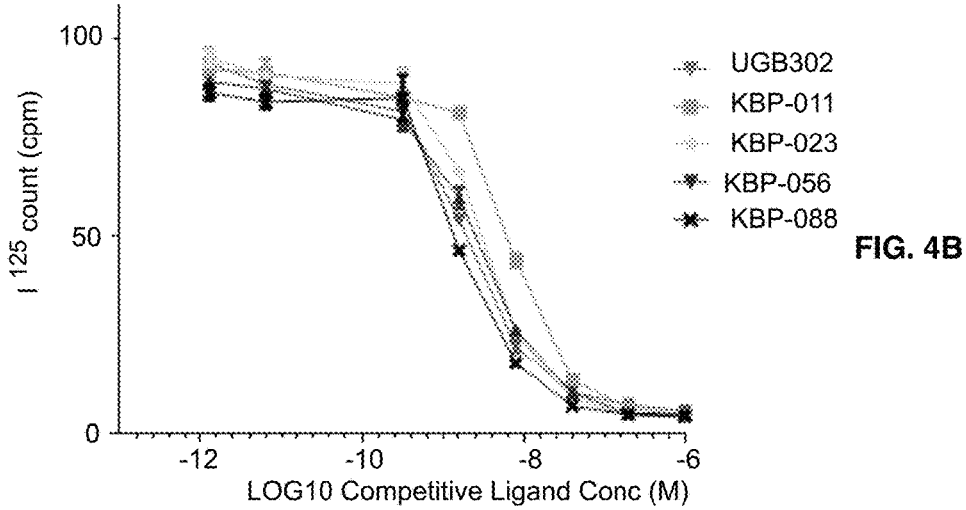

FIGS. 4A-4B: Competitive binding of tested compounds on U20S-CALCR cells expressing the CTR (FIG. 4A) and CHO-K1CALCRRAMP3 cells expressing the AMY-R (FIG. 4B), with pIC50 figures in the table.

Figure 5:
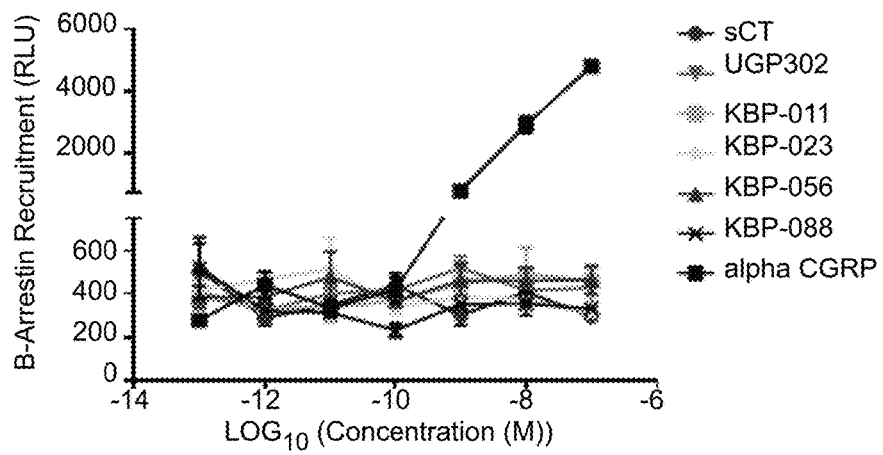

FIG. 5: Dose-response activation of the CGRP-R for the different ligands.

Figure 6A:
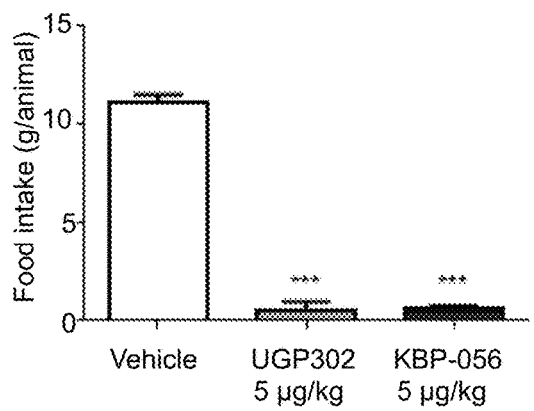
Figure 6C:
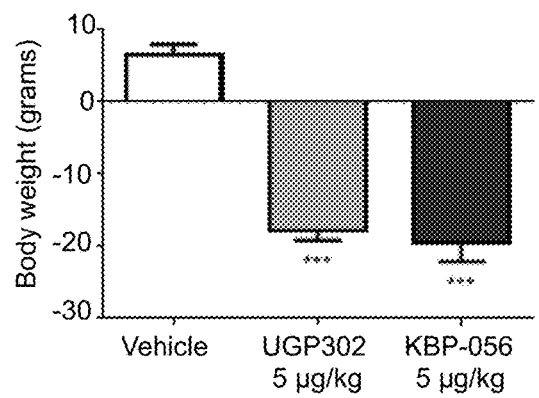
Figure 6B:
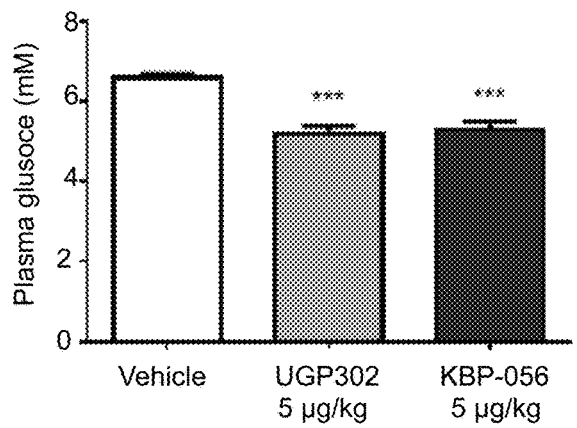

FIGS. 6A-6C: The effect of a single dose of KBP-056 on food intake (FIG. 6A), bodyweight (FIG. 6B) and PPG (FIG. 6C).

Figure 7A:
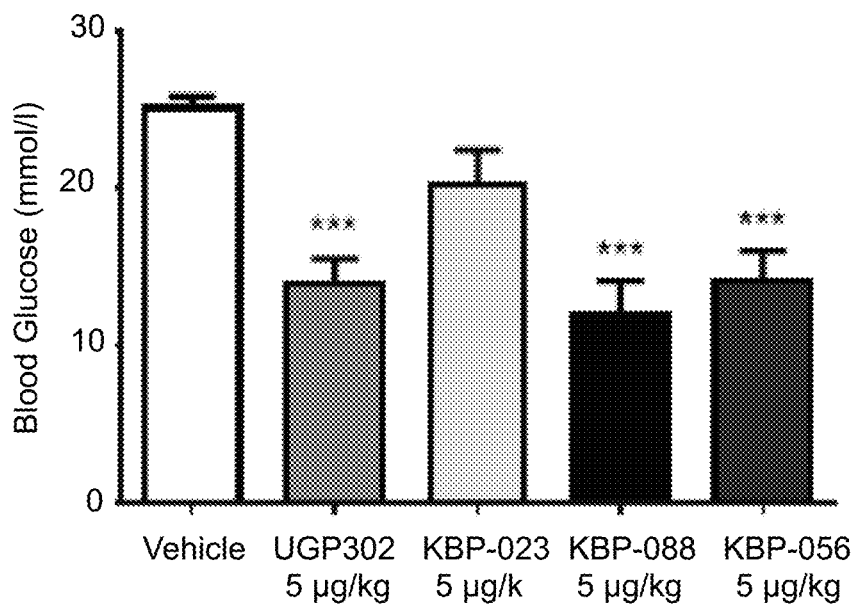
Figure 7B:
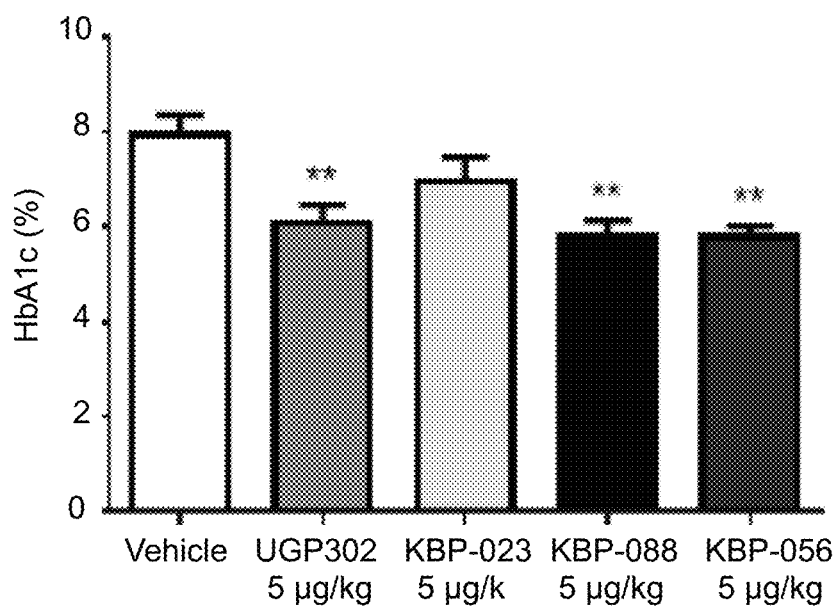

FIGS. 7A-7B: The effect of three weeks of treatment with UGP302/KBP-042, KBP-023, KBP-056 and KBP.088 on FPG (FIG. 7A) and HbA1c (FIG. 7B).

Figure 8A:
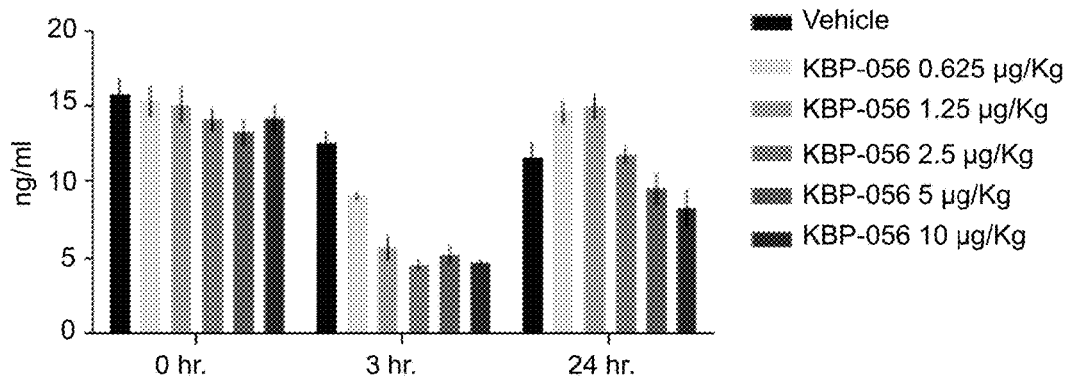
Figure 8B:
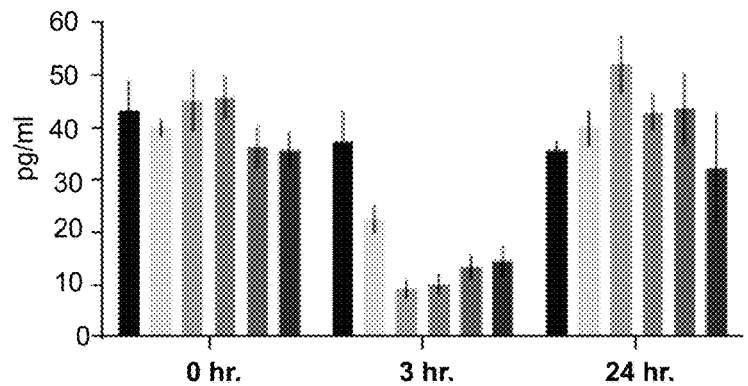

FIGS. 8A-8B: The effect of the KBP compounds on resorption of type I collagen, (FIG. 8A) and on resorption of type II collagen (FIG. 8B).

Figure 9:
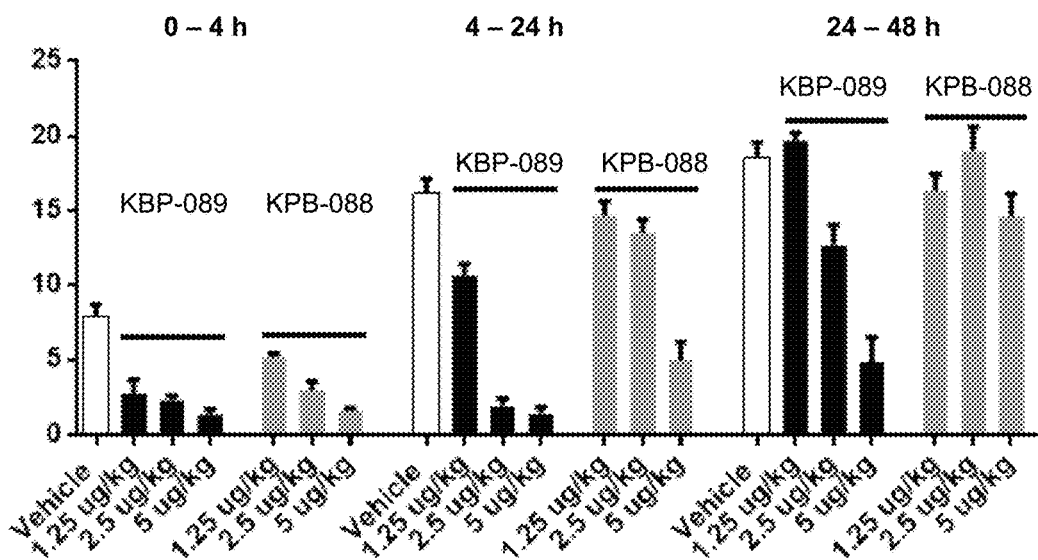

FIG. 9: Results obtained in Example 7 of a comparison between the effects of compounds KBP-088 and KBP-089 on food intake in obese rats.

Figure 10:
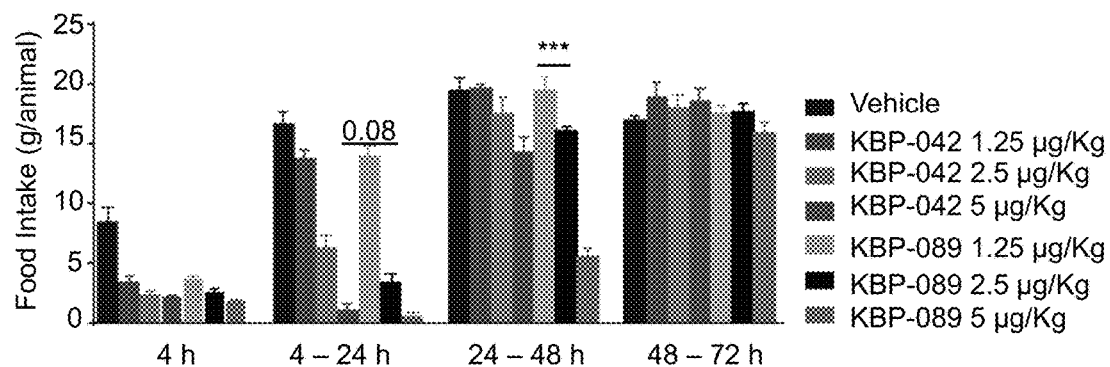

FIG. 10: Short term food intake measurements obtained in Example 7 in a comparison between peptide KBP-089 of the invention and known peptide KBP-042.

Figure 11A:
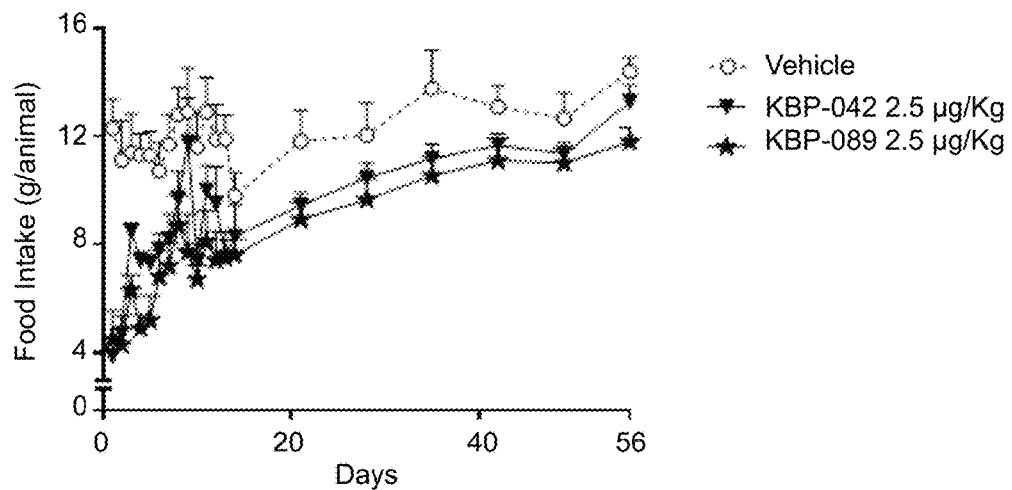
Figure 11B:
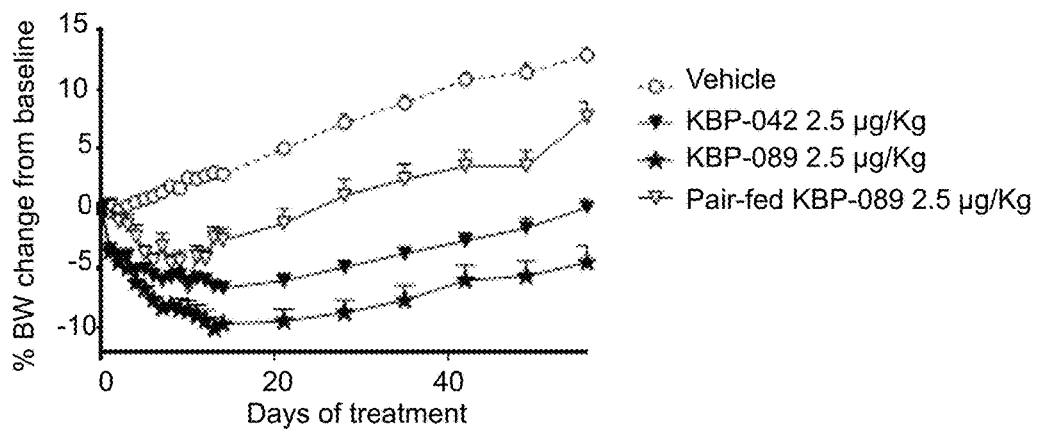

FIGS. 11A-11B: Long term food intake measurements (FIG. 11A) and body weight change (FIG. 11B) for KBP-089 and KBP-042 peptides.

Figure 12A:
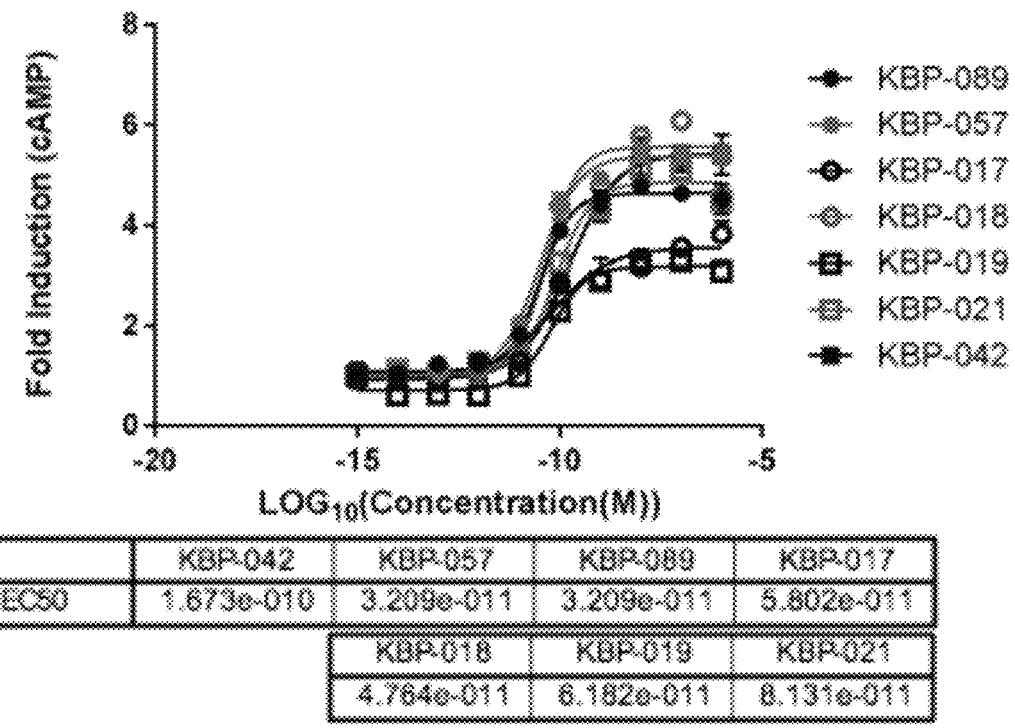
Figure 12B:
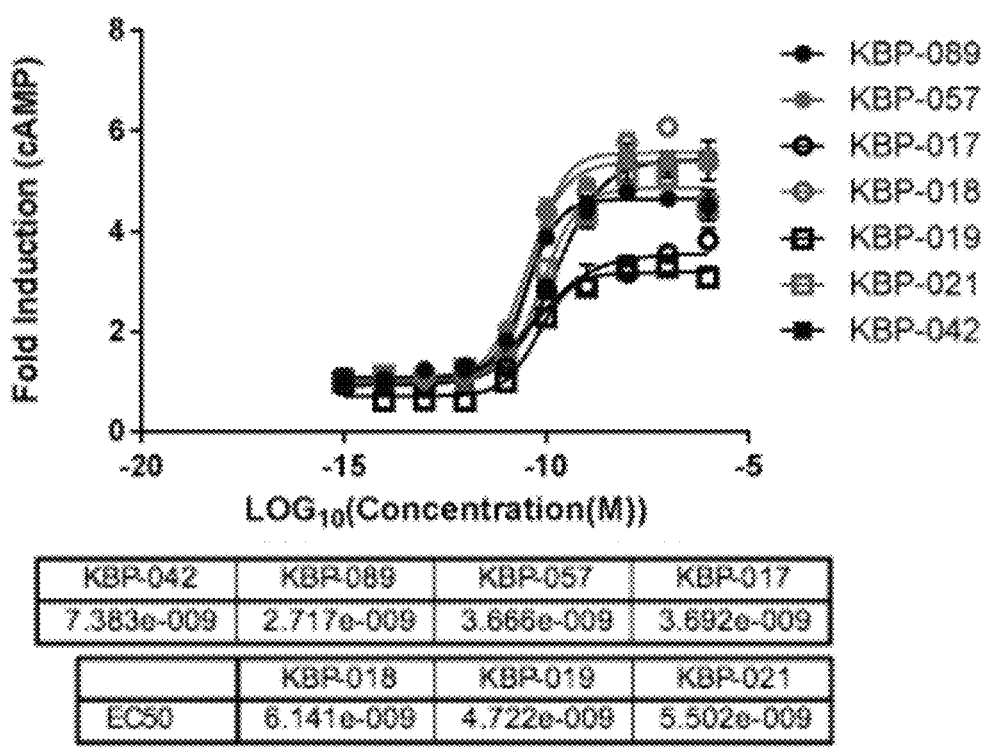
Figure 12C:
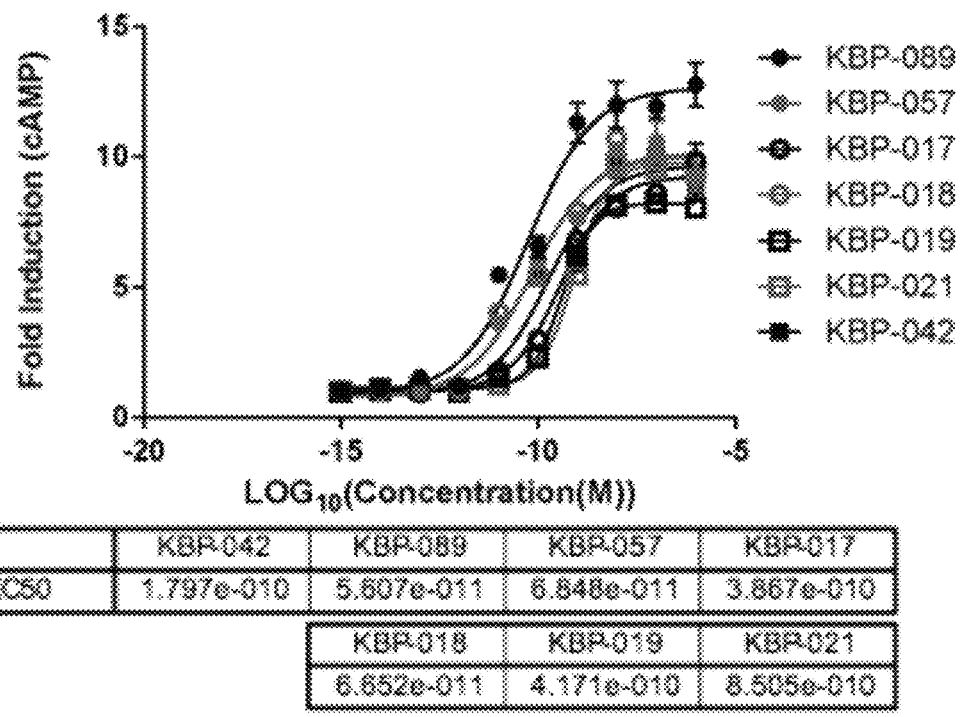
Figure 12D:
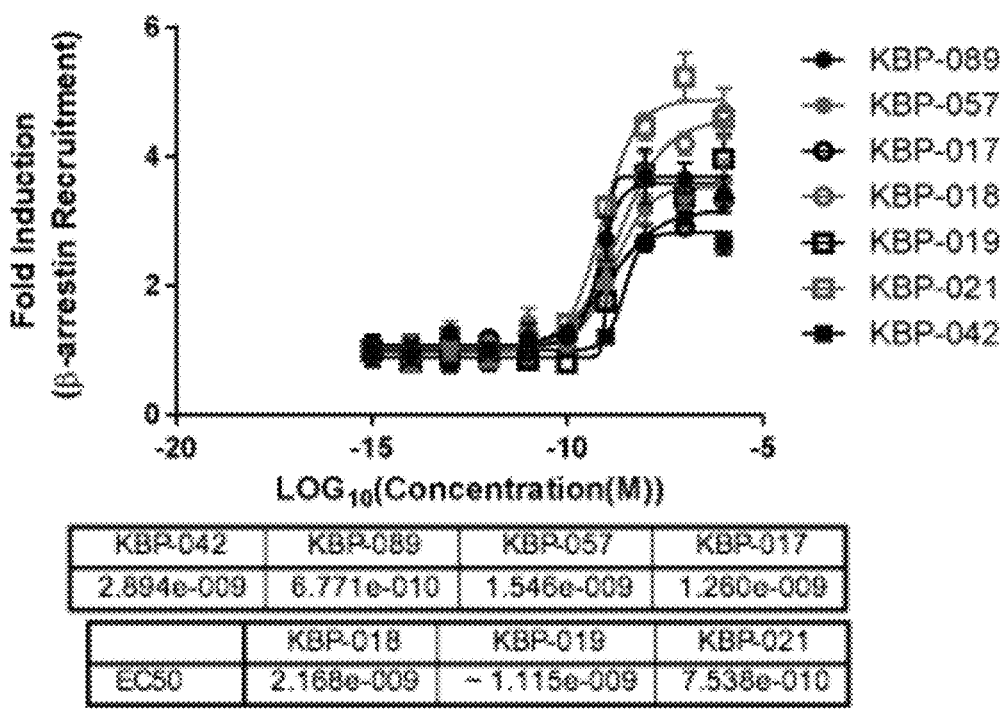
Figure 12E:
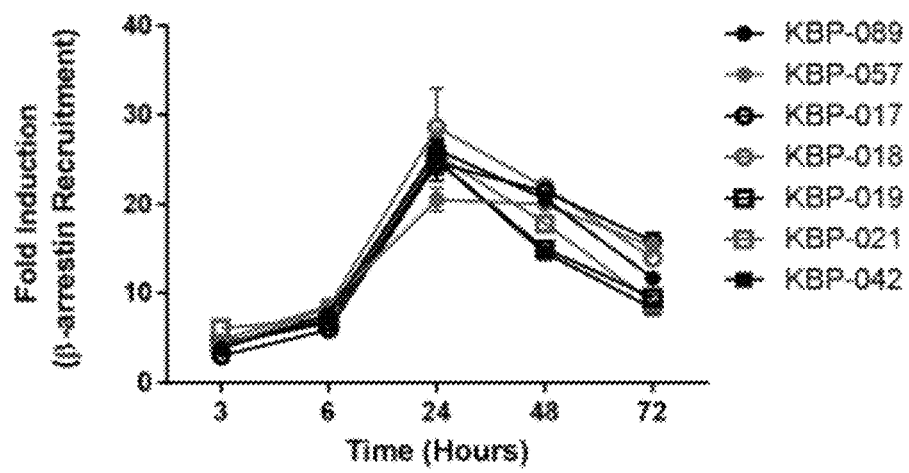
Figure 12F:
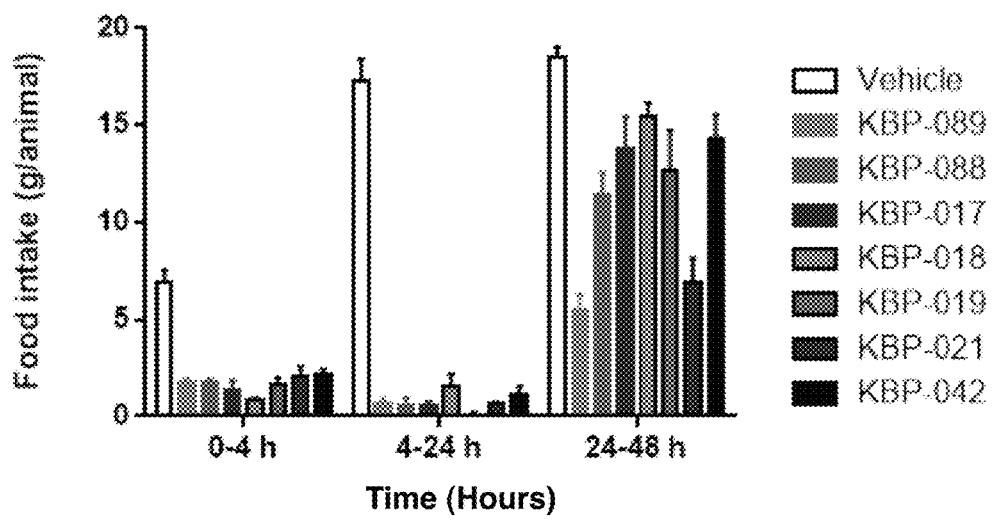

FIGS. 12A-12F: Further results obtained in Example 1 for cAMP induction by action on the calcitonin receptor (FIGS. 12A, 12B and 12E) and on the amylin receptor (FIGS. 12D and 12E) and further results obtained in Example 7 in food intake measurements (FIG. 12F).

EXAMPLES

In the following examples, the following materials and methods were employed.

Cells and Cell Lines

The following cell lines expressing the calcitonin, amylin and CGRP receptors were purchased and cultured according to the manufacturer's instructions.
1. Calcitonin Receptor (CTR): U20S-CALCR from DiscoveRx (Cat. No.: 93-0566C3).
2. Amylin Receptor (AMY-R): CHO-K1 CALCR+ RAMP3 from DiscoveRx (Cat. No.: 93-0268C2).
3. CGRP Receptor (CGRP-R): CHO-K1 CALCRL+ RAMP1 from DiscoveRx (Cat. No.: 93-0269C2).

In independent bioassays, CTR, AMY-R and CGRP-R cells were treated with for the indicated timepoints with increasing doses of sCT, UGP-302/KBP-042 or the KBPs identified in Table 3 (0, 0.001, 0.01, 0.1, 1, 10, and 100 nM).

Example 1: β-Arrestin Assay

PathHunter β-Arrestin GPCR assays are whole cell, functional assays that directly measure the ability of a ligand to activate a GPCR by detecting the interaction of β-Arrestin with the activated GPCR. Because Arrestin recruitment is independent of G-protein signaling, these assays offer a powerful and universal screening and profiling platform that can be used for virtually any Gi-, Gs, or Gq-coupled receptor.

In this system, the GPCR is fused in frame with the small enzyme fragment ProLink™ and co-expressed in cells stably expressing a fusion protein of β-Arrestin and the larger, N-terminal deletion mutant of β-gal (called enzyme acceptor or EA). Activation of the GPCR stimulates binding of β-Arrestin to the ProLink-tagged GPCR and forces complementation of the two enzyme fragments, resulting in the formation of an active β-gal enzyme. This interaction leads to an increase in enzyme activity that can be measured using chemiluminescent PathHunter® Detection Reagents.

The assay was performed in white 384 well plates (Greiner Bio-One, 784080). Cells were seeded 2500 cells per well in 10 μL cell-type specific medium the day prior to the experiment. To quantify the GPCR-mediated β-arrestin recruitment the Pathhunter™ Detection Kit (93-0001, DiscoverX) was used and assay performed accordingly to the manufacturer's instructions.

Results are seen in FIGS. 1A-1E, 2A-2B and 3. As seen in FIGS. 1A-1E, the peptides are quite similar in activity; however, with increasing time KBP-056 shows a superior ability to activate and maintain activation of the CTR. This is even better illustrated in FIGS. 2A-2B, where the individual ligands are plotted at one given concentration and as a function of time. Here it is apparent that KBP-056 is superior to the other peptides in terms of calcitonin receptor activation.

Another important trait of this class of molecules is the ability to activate the amylin receptor AMY-R, and as seen in FIG. 3, the KBPs are fully capable of activating this receptor, and KBP-088 is more potent that the classical AMY-R agonist sCT.

In a subset of the figures, the beta-arrestin assay was used to assess prolonged receptor activation. This was done using the Calcitonin Receptor (CTR): U20S-CALCR from DiscoveRx (Cat. No.: 93-0566C3) cell line, and as opposed to the classical 3 hour output, beta-arrestin accumulation was conducted over 24, 48 and 72 hour and then analyzed.

Peptides for use in the invention were ranked in terms of their ability to activate the CTR and AMY-R in vitro in decreasing order, as follows:

| Intervention | 4 h | 24 h | 48 h | RANK (4 h) | RANK (24 h) | RANK (48 h) |
|---|---|---|---|---|---|---|
| KBP-089 | 1.8 | 0.7 | 5.4 | + | + | + |
| KBP-021 | 2.1 | 0.6 | 6.9 | + | + | + |
| KBP-019 | 1.3 | 0.2 | 11.8 | + | + | + |
| KBP-088 | 1.9 | 0.4 | 11.4 | + | + | + |
| KBP-042* | 2.2 | 1.2 | 14.3 | + | + | 0 |
| nf-hCT* | 2.7 | 15.9 | 15.9 | + | 0 | 0 |
| Vehicle* | 8.5 | 16.6 | 19.3 | 0 | 0 | 0 |

*Comparative

Example 2: Competitive Ligand Binding

In this Example we demonstrate the relative abilities of test compounds to bind the calcitonin and amylin receptors. Corresponding to the beta-arrestin induction experiments, we performed competitive ligand binding experiments using the cells expressing the CTR and the AMY-R. In studying ligand binding on cells, 15.000 CTR or AMY-R cells were seeded in 96-well plate and cells were treated with 0.1 nM $^{125}$I-conjugated sCT with or without the presence of unlabelled KBP in increasing doses for 60 min at 37° C. After incubation the supernatant was removed and cells were washed twice in 200 µl PBS. The cells were lysed using RIPA‡ buffer (30 mM M NaCl, 50 mM Tris-HCl, 5 mM EDTA, 1% Deoxycholic acid, 10% SDS, Protease inhibitor tablet mini (1 tablet:10 ml)) and lysates as well were collected for measurement on a γ-counter.

Results are seen in FIGS. 4A-4B. Firstly, we found that all ligands bound potently to both receptors; however, in terms of affinity KBP-088 was better than the other ligands, particularly on the AMY-R.

Example 3: β-Arrestin Recruitment Tested on the CGRP-Receptor

As peptides with the ability to activate the amylin receptor have been shown to activate the CGRP-R, an effect which may be detrimental to the overall effect of the compounds, we assessed whether the KBPs activated the CGRP-receptor. As seen in FIG. 5, unlike salmon calcitonin, none of the KBP compounds activated the CGRP-R.

Example 4: In Vivo Activity Test on Bodyweight

To ensure the in vivo activity of this class of peptides, an acute test of the ability of KBP-056 to reduce food intake, bodyweight and post-prandial glucose compared to UGP302/KBP-042 was conducted. Male Sprague-Dawley rats were fed high fat diet for 8 weeks to induce obesity, and were then exposed to a single subcutaneous dose of 5 µg/kg KBP-056, UGP302/KBP-042 or vehicle (saline) (5 rats per group), and the effect on food intake, bodyweight and blood glucose was assessed. Blood was collected from the tail vein after 18 hours of dosing. Whole blood glucose levels were determined with an ACCU-CHEK® Avia blood glucose meter (Roche Diagnostics, Rotkreuz, Switzerland).

As seen in FIGS. 6A-6B, KBP-056 strongly reduced food intake over an 18-hour period (FIG. 6A), which is also manifested in a significant weight loss (FIG. 6B). Interestingly, the weight loss appears to exceed that caused by UGP302/KBP-042. Finally, a prominent reduction in postprandial glucose levels (FIG. 6C) was observed, thereby confirming that this novel class of peptides shows substantial in vivo activity.

Example 5: In Vivo Activity Test on Fasting Plasma Glucose and HbA1c

To assess the effects of the peptides in relation to regulation of blood glucose levels, male ZDF rats, which are the gold standard model of Type 2 Diabetes were treated for 3 weeks with the 3 most promising KBPs (023, 056 and 088) and an active comparator (UGP302/KBP-042). Male ZDF (fa/fa) rats were obtained at the age of 7 weeks from Charles River Laboratories (Kisslegg, Deutschland). All animals were housed at the animal facility at Nordic Bioscience with a constant temperature (21-23° C.) and relative humidity (55-65%) on a 12 h light/dark cycle with free access to Purina 5008 rat chow (Brogaarden, Lynge, Denmark) and tap water. At the age of 8 weeks, the animals were randomized into five groups of 8 rats each based upon fasting blood glucose and body weight (Vehicle (saline), UGP302/KBP-042 5 µg/kg/day, KBP-023 5 µg/kg/day, KBP-056 5 µg/kg/day and KBP-088 5 µg/kg/day) and dosing was done subcutaneously once daily. The animals were treated for a total of 3 weeks to assess the effect of the peptides on fasting blood glucose. Blood glucose was monitored using the Accu-Check® Avia monitoring system (Roche Diagnostics, Rotkreuz, Switzerland) and HbA1c levels by the DCA Vantage™ Analyzer (Siemens Healthcare Diagnostics, Deerfield, Ill.).

Fasting blood glucose and HbA1c were assessed after three weeks, and as seen in FIGS. 7A-7B, both KBP-056 and KBP-088 were highly active with respect to reduction of FPG and HbA1c, and interestingly they appeared superior to UGP302/KBP-042, indicating that the aminoacid substitutions improve efficacy, as also seen in the in vitro data.

Example 6: The Effect of KBP-056 on Bone Resorption and Cartilage Degradation

In view of the relationship between the KBPs and different calcitonins, and the well-known bone and cartilage protective effects of salmon calcitonin, the effects of KBP-056 on bone resorption (measured by CTX-I) and cartilage degradation (Assessed by CTX-II) were analyzed in male rats on HFD. As seen in FIGS. 8A-8B KBP-056 dose and time-dependently reduced both CTX-I (FIG. 8A) and CTX-II (FIG. 8B), with maximum inhibition reached three hours after dosing and at doses exceeding 1 µg/kg/day. This confirmed that the KBPs maintain their beneficial effects on bone and cartilage despite the amino-acid changes. Further-more, based on their superiority in other tests, we expect these effects to be superior as well.

Example 7: Comparative Effect of KBP 088 and KBP 089 on Food Intake in Obese Rats Rats were fed a High-Fat-Diet for 14 weeks prior to the experiment to induce obesity. They were then randomized into groups (Vehicle (0.9% NaCl), KBP-089 (doses: 1.25, 2.5, 5 µg/kg) and KBP-088 (doses: 1.25, 2.5, 5 µg/kg). They were fasted overnight and then treated with a single dose of peptide or vehicle in the morning using subcutaneous administration. The food intake was monitored in the following intervals (0-4 hours, 4-24 hours and 24-48 hours). As seen in FIG. 9, both KBP-088 and KBP-089 led to a reduction in food intake within the 4 hour interval, and the effect was maintained to 24 hours. In the interval between and 48 hours only KBP-089 led to a reduction in food intake indicating that this molecule is superior to KBP-088.

In FIG. 12F, similar test results are shown for a wider range of peptides according to the invention.

Further similar studies were undertaken over different time periods and with different peptides and the results are seen in FIG. 10 and FIGS. 11A-11B. The ability of KBP089 to suppress food intake over 72 hours was compared to that of KBP042 as control and the results are seen in FIG. 10.

To further investigate the potency of KBP-089 against KBP-042 obese rats were dosed with 2.5 µg/kg/day given as subcutaneous injection of either KBP-089 or KBP-042 and then two control groups, a vehicle and a calorie restriction group, in which the food intake was matched to the food intake of the KBP-089 group to shed light on whether effects independent of food intake could be observed.

In FIGS. 11A-11B; the effect of the peptides on food intake (FIG. 11A) and bodyweight (FIG. 11A) during the eight week treatment period is shown in the upper and lower panels respectively. As can be seen both peptides reduce food intake dramatically in the beginning as expected, after which the effect is reduced and the food intake gradually normalizes. The effect on bodyweight is shown in FIG. 11B, lower panel, where it is clearly seen that both peptides cause a substantial weight loss; however, the weight loss introduced by KBP-089 is greater than that introduced by KBP-042 showing superiority. Additionally, when comparing KBP-089 to the calorie restricted control group (pair-fed), which has received exactly the same amount of food as the KBP-089 group over the study period, it is clear that the weight reduction is not only mediated by a restriction of food intake, but also by other effects.

In this specification, unless expressly otherwise indicated, the word 'or' is used in the sense of an operator that returns a true value when either or both of the stated conditions is met, as opposed to the operator 'exclusive or' which requires that only one of the conditions is met. The word 'comprising' is used in the sense of 'including' rather than in to mean 'consisting of'. All prior teachings acknowledged above are hereby incorporated by reference. No acknowledgement of any prior published document herein should be taken to be an admission or representation that the teaching thereof was common general knowledge in Australia or elsewhere at the date hereof.

The invention claimed is:

1. A peptide comprising the amino acid sequence of SEQ ID NO: 43.

2. The peptide as claimed in claim 1, consisting of the amino acid sequence of SEQ ID NO: 44.

3. The peptide as claimed in claim 1, formulated for enteral administration.

4. The peptide as claimed in claim 1, formulated for parenteral administration.

5. The peptide as claimed in claim 4, formulated for injection.

6. The peptide as claimed in claim 1, formulated with a carrier for oral administration.

7. The peptide as claimed in claim 6, wherein the carrier comprises N-(5-chlorosalicyloyl)-8-aminocaprylic acid (5-CNAC), sodium salt of 10-(2-Hydroxybenzamido)decanoic acid (SNAD), or sodium salt of N-(8-[2-hydroxybenzoyl]amino)caprylic acid (SNAC).

8. The peptide of claim 1, wherein the peptide is carboxylated at its N-terminal.

9. The peptide of claim 1, wherein the peptide is amidated at its C-terminal.

10. A pharmaceutical composition comprising the peptide of claim 1 coated with citric acid particles wherein the coated citric acid particles increase the oral bioavailability of the peptide.

11. A method for treating Type II diabetes, obesity, osteoporosis, osteoarthritis, or improving glycemic control, comprising administering the peptide as claimed in claim 1.

12. A method for treating Type II diabetes, obesity, osteoporosis, osteoarthritis, or improving glycemic control, comprising administering the peptide as claimed in claim 1 in conjunction with metformin or another insulin sensitizer.

* * * * *